United States Patent [19]

Birch et al.

[11] Patent Number: 5,627,191

[45] Date of Patent: May 6, 1997

[54] THERAPEUTIC AGENTS

[75] Inventors: Alan M. Birch; Robert W. Steele; Barbara W. Hitchin; John P. Watts, all of Nottingham, England

[73] Assignee: The Boots Company PLC, Notts, England

[21] Appl. No.: 362,492

[22] PCT Filed: Jul. 3, 1993

[86] PCT No.: PCT/EP93/01774

§ 371 Date: Feb. 21, 1995

§ 102(e) Date: Feb. 21, 1995

[87] PCT Pub. No.: WO94/01436

PCT Pub. Date: Jan. 20, 1994

[30] Foreign Application Priority Data

| Jul. 10, 1992 | [GB] | United Kingdom | 9214690 |
| Aug. 29, 1992 | [GB] | United Kingdom | 9218449 |
| Sep. 5, 1992 | [GB] | United Kingdom | 9218848 |
| Sep. 5, 1992 | [GB] | United Kingdom | 9218849 |

[51] Int. Cl.$^6$ .................. A61K 31/435; C07D 471/04
[52] U.S. Cl. ........................................ 514/303; 546/118
[58] Field of Search ............................ 546/118; 514/303

[56] References Cited

U.S. PATENT DOCUMENTS

| 5,049,565 | 9/1991 | Chen et al. | 514/302 |
| 5,057,522 | 10/1991 | Chen et al. | 514/303 |
| 5,066,586 | 11/1991 | Chen et al. | 435/119 |
| 5,087,702 | 2/1992 | Chen et al. | 546/118 |
| 5,102,880 | 4/1992 | Chakravarty et al. | 514/212 |
| 5,124,335 | 6/1992 | Patchett et al. | 514/300 |
| 5,128,327 | 7/1992 | Chakravarty et al. | 514/81 |
| 5,157,026 | 10/1992 | Chakravarty et al. | 514/81 |
| 5,330,989 | 7/1994 | Soll et al. | 514/258 |
| 5,332,744 | 7/1994 | Chakravarty et al. | 514/265 |

FOREIGN PATENT DOCUMENTS

| 099122 | 1/1984 | European Pat. Off. . |
| 400974 | 12/1990 | European Pat. Off. . |
| 415886 | 3/1991 | European Pat. Off. . |
| 420237 | 4/1991 | European Pat. Off. . |
| 426379 | 5/1991 | European Pat. Off. . |
| 426021 | 5/1991 | European Pat. Off. . |
| 434038 | 6/1991 | European Pat. Off. . |
| 461040 | 12/1991 | European Pat. Off. . |
| 467715 | 1/1992 | European Pat. Off. . |
| 470543 | 2/1992 | European Pat. Off. . |
| 503838 | 9/1992 | European Pat. Off. . |
| 510813 | 10/1992 | European Pat. Off. . |
| 513979 | 11/1992 | European Pat. Off. . |
| 533058 | 3/1993 | European Pat. Off. . |
| 2673943 | 9/1992 | France . |
| 4031601 | 4/1992 | Germany . |
| 91/11999 | 8/1991 | WIPO . |

*Primary Examiner*—Bernard Dentz
*Attorney, Agent, or Firm*—Nikaido, Marmelstein, Murray & Oram LLP

[57] ABSTRACT

The invention provides compounds of formula I

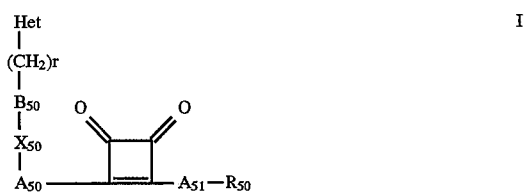

and pharmaceutically acceptable salts thereof; wherein $R_{50}$ is hydrogen or $C_{1-4}$ alkyl, $A_{51}$ is oxygen, sulphur or a group of the formula —$NR_{52}$— wherein $R_{52}$ is hydrogen or $C_{1-4}$ alkyl; $A_{50}$ comprises i) a mono or bicyclic aromatic ring optionally containing one or more nitrogen, oxygen or sulphur atoms, ii) a cycloalkendiyl group, or iii) an acyclic bridging group having a chain of one, two or three atoms between the cyclobutenedione group and $X_{50}$, said chain being a chain of one or two carbon atoms or a chain of one carbon atom and one or more nitrogen, oxygen or sulphur atoms or iv) a bond; $X_{50}$ is either a bond or a spacer group providing a chain between $A_{50}$ and $B_{50}$ of one or two atoms length; $B_{50}$ is a mono or bicyclic aromatic-ring optionally containing one or more nitrogen, oxygen or sulphur atoms; r is an integer from 1 to 6; and Het is a ring system optionally containing one or more nitrogen, oxygen or sulphur atoms or is a phosphonate, phosphinate or amine derivative (wherein each of $A_{50}$, $X_{50}$, $B_{50}$ and Het are optionally substituted).

The compounds have angiotensin II antagonist activity and are useful in the treatment of cardiovascular disorders such as hypertension.

5 Claims, No Drawings

THERAPEUTIC AGENTS

This application is a 371 of PCT/EP93/01774 filed Jul. 3, 1993.

The present invention relates to novel therapeutic agents and, in particular, to novel substituted cyclobut-3-ene-1,2-diones, to processes for their preparation, to pharmaceutical compositions containing them and to their therapeutic activity in the treatment of cardiovascular diseases.

Angiotensin II is a key mediator of the reninangiotensin system. It is known that angiotensin II is an arterial vasconstrictor that exerts its action by interacting with specific receptors on cell membranes. Recently, several non-peptide compounds have been reported as angiotensin II antagonists and as useful antihypertensive agents.

The present invention provides compounds of formula I

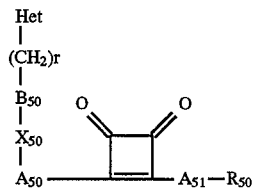

and pharmaceutically acceptable sales thereof; wherein $R_{50}$ is hydrogen or $C_{1-4}$ alkyl, $A_{51}$ is oxygen, sulphur or a group of the formula —$NR_{52}$— wherein $R_{52}$ is hydrogen or $C_{1-4}$ alkyl; $A_{50}$ comprises i) a mono or bicyclic aromatic ring optionally containing one or more nitrogen, oxygen or sulphur atoms, ii) a cycloalkendiyl group, iii) an acyclic bridging group having a chain of one, two or three atoms between the cyclobutenedione group and $X_{50}$, said chain being a chain of one or two carbon atoms or a chain of one carbon atom and one or more nitrogen, oxygen or sulphur atoms or iv) a bond; $X_{50}$ is either a bond or a spacer group providing a chain between $A_{50}$ and $B_{50}$ of one or two atoms length; $B_{50}$ is a mono or bicyclic aromatic ring optionally containing one or more nitrogen, oxygen or sulphur atoms; r is an integer from 1 to 6; and Het is a ring system optionally containing one or more nitrogen, oxygen or sulphur atoms or is a phosphonate, phosphinate or amine derivative (wherein each of $A_{50}$, $X_{50}$, $B_{50}$ and Het are optionally substituted).

Preferably, $A_{50}$ is a group selected from the groups represented by (i) to (xii) below (wherein in each case $Z_{50}$ is a bond to $X_{50}$ and the other free valency is connected to the cyclobutenedione group).

(i)

wherein $R_{70}$ and $R_{71}$ are each independently hydrogen, hydroxy, alkyl (optionally substituted by halo, $C_{3-8}$ cycloalkyl or phenyl), $C_{3-12}$ cycloalkyl or phenyl (both optionally substituted by halo, $C_{1-6}$ alkyl or $C_{1-6}$ alkoxy) or $R_{70}$ and $R_{71}$ together complete a 3 to 7 membered carbocycle (optionally substituted by one or two $C_{1-6}$ alkyl, $C_{1-6}$ alkoxy, phenyl, hydroxy or halo groups);

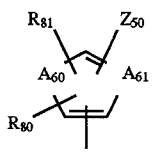

(ii)

wherein $A_{60}$ is nitrogen or methine; $A_{61}$ is imino, oxygen or sulphur and either $R_{80}$ and $R_{81}$ are each independently hydrogen, halo, fluoro, nitro, cyano, alkyl $C_{2-10}$ (preferably $C_{2-4}$)alkenyl, alkylthio, mono-, di- or trihalo-($C_{1-6}$ alkyl), hydroxyalkyl, oxoalkyl, carboxy or esterified carboxy, or, when $R_{80}$ and $R_{81}$ are on adjacent carbon atoms, $R_{80}$ and $R_{81}$ together may be 1,3-butadienylene thereby completing a fused aromatic ring;

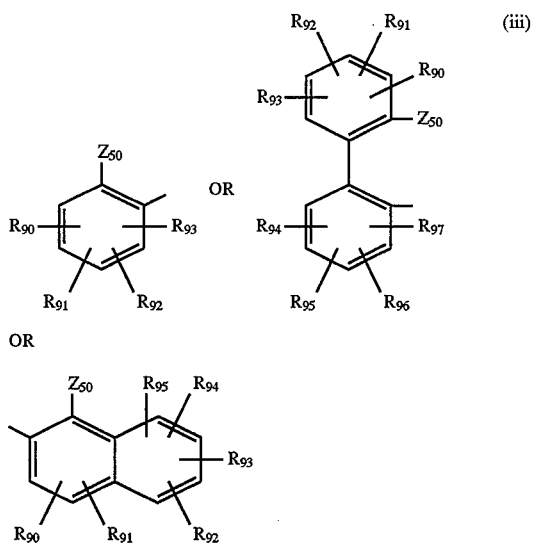

(iii)

wherein $R_{90}$ to $R_{97}$ are each independently hydrogen, halo, fluoro, nitro, amino, $C_{1-4}$ alkylamino, di($C_{1-4}$ alkyl)amino, trifluoromethyl, $C_{1-4}$ alkyl, $C_{1-4}$alkoxy or a group of the formula —$SO_2NHR_{98}$ (wherein $R_{98}$ is hydrogen, $C_{1-5}$ alkyl, aryl or arylmethyl);

(iv)

wherein —$A_{70}$—$A_{71}$—$A_{72}$—$A_{73}$— is a group of formula —$NC(R_{100})C(R_{101})C(R_{102})$—, —$C(R_{100})NC(R_{101})C(R_{102})$—, —$C(R_{100})C(R_{101})NC(R_{102})$—, —$C(R_{100})C(R_{101})C(R_{102})N$—, —$NC(R_{100})NC(R_{101})$—, —$C(R_{100})NC(R_{101})N$—, —$NNC(R_{100})C(R_{101})$—, —$C(R_{100})NNC(R_{101})$—, —$C(R_{100})C(R_{101})NN$—, —$NC(R_{100})C(R_{101})N$—, —$C(R_{100})C(R_{101})C(O)N(R_{103})$—, —$C(R_{100})C(R_{101})N(R_{103})C(O)$—, —$C(O)N(R_{103})C(R_{100})C(R_{101})$—, —$N(R_{103})C(O)C(R_{100})C(R_{101})$—, —$C(O)N(R_{103})C(R_{100})N$—, —$C(R_{100})NC(O)N(R_{103})$—, —$N(R_{103})C(O)NC(R_{100})$—, —$NC(R_{100})N(R_{103})C(O)$—, —$C(O)N(R_{103})NC(R_{100})$— or —$C(R_{100})NN(R_{103})C(O)$—; wherein $R_{100}$ to $R_{102}$ are each independently hydrogen, halo, fluoro, nitro, amino, $C_{1-4}$ alkylamino, di($C_{1-4}$alkyl)amino, trifluoromethyl, $C_{1-4}$ alkyl, $C_{1-4}$alkoxy or a group of the formula $SO_2NHR_{104}$ (wherein $R_{104}$ is hydrogen, $C_{1-6}$ alkyl, aryl, arylmethyl or a group of formula —$CH_2OC(O)CH_3$) or, when two of $R_{100}$, $R_{101}$ and $R_{102}$ are bonded to adjacent carbon atoms, they may be joined to form a fused phenyl or naphthyl ring; and $R_{103}$ is hydrogen, $C_{1-4}$ alkyl, phenyl or phenylmethyl (in which the phenyl or phenylmethyl is optionally substituted with one or two substituents selected from halo, fluoro, $C_{1-4}$ alkyl, $C_{1-4}$ alkoxy, trifluoromethyl, amino, $C_{1-4}$alkylamino, di($C_{1-4}$ alkyl)amino or a group of formula —$CO_2R_{104}$ (wherein $R_{104}$ is as defined above));

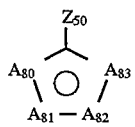

(v)

wherein —$A_{80}$—$A_{81}$—$A_{82}$—$A_{83}$— is a group of formula —$Y_{50}$—$C(R_{110})C(R_{111})C(Z_{52})$—, —$C(R_{110})Y_{50}C(R_{111})C(Z_{52})$—, —$C(R_{110})C(R_{111})Y_{50}C(Z_{52})$—, —$Y_{50}C(R_{110})C(Z_{52})C(R_{111})$—, —$C(R_{110})Y_{50}C(Z_{50})C(R_{111})$— or —$C(R_{110})C(R_{111})C(Z_{52})Y_{50}$—, wherein $Y_{50}$ is oxygen, sulphur, sulphinyl or sulphonyl; $R_{110}$ and $R_{111}$ are each independently hydrogen, halo, fluoro, nitro, amino, formyl, $C_{1-4}$ alkylamino, di($C_{1-4}$ alkyl)amino, trifluoromethyl, $C_{1-7}$ alkyl, $C_{1-6}$ alkoxy, $C_{3-7}$ cycloalkyl, or a group of formula —$SO_2NHR_{112}$, —$(CH_2)_cO(CH_2)_dCH_3$, —$(CH_2)_dO(CH_2)_dCH_3$, —$(CH_2)N(R_{112})_2$, —$CH(OR_{112})(C_{1-7}$ alkyl), —$CO_2R_{112}$, —$CH=CHR_{112}$, —$CH_2CR_{112}=C(R_{112})_2$, —$(CH_2)_eNHC(O)R_{112}$ —$(C_{1-4})$alkylaryl or —$CH(R_{112})_2$ (wherein $R_{112}$ is hydrogen, $C_{1-6}$ alkyl, arylmethyl or aryl, c is an integer from about 1 to 3, d is an integer from 1 to 5 and e is 0 or an integer from 1 to 2) or, when $R_{110}$ and $R_{111}$ are bound to adjacent carbon atoms, they may be joined to form a phenyl or naphthyl ring; and wherein $Z_{52}$ represents the "other" free valency referred to above;

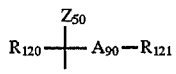

(vi)

wherein $A_{90}$ is a bond, oxygen, sulphur, sulphinyl, sulphonyl, methylene or a group of the formula —$NR_{122}$— (wherein $R_{122}$ is hydrogen, $C_{1-6}$ alkyl, aryl, aryl($C_{2-7}$)alkylcarbonyl, ($C_{1-6}$)alkylcarbonyl, [($C_{2-5}$)alkenyl]methylene, [($C_{2-5}$)alkynyl]methylene or arylmethylene); and $R_{120}$ and $R_{121}$ are each independently hydrogen, $C_{1-6}$ alkyl (optionally substituted with aryl or $C_{3-7}$ cycloalkyl), aryl (optionally substituted with up to five substituents selected from halo, fluoro, $C_{1-6}$ alkyl, ($C_{2-5}$ alkenyl)methylene, ($C_{2-5}$ alkynyl)methylene, $C_{1-5}$ alkoxy, $C_{1-5}$ alkylthio, nitro, trifluoromethyl, hydroxy, nitro, or a group of formula —$CO_2R_{123}$ (wherein $R_{123}$ is hydrogen, $C_{1-6}$ alkyl, aryl or arylmethylene)), or aryl-($C_{1-2}$)alkyl, (optionally substituted with up to 5 substituents selected from halo, fluoro, $C_{1-6}$ alkyl, ($C_{2-5}$alkenyl)methylene, ($C_{2-5}$alkynyl) methylene, $C_{1-5}$ alkoxy, $C_{1-5}$alkylthio, nitro, trifluoromethyl, hydroxy or group of formula —$CO_2R_{123}$ (wherein $R_{123}$ is defined above)), or $C_{3-7}$ cycloalkyl.

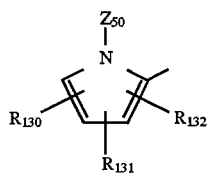

(vii)

wherein $R_{130}$, $R_{131}$ and $R_{132}$ are each independently hydrogen, halo, fluoro, nitro, amino, $C_{1-4}$alkylamino, di($C_{1-4}$ alkyl)amino, trifluoromethyl, $C_{1-4}$ alkyl, $C_{1-4}$ alkoxy or a group of the formula —$SO_2NHR_{133}$ (wherein $R_{133}$ is hydrogen, $C_{1-5}$ alkyl, aryl or arylmethyl);

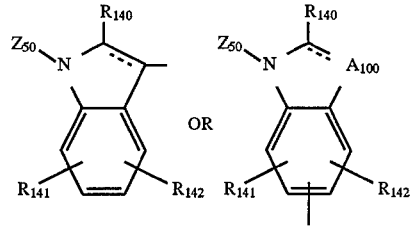

(viii)

OR

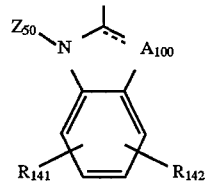

wherein $R_{140}$ is hydrogen, alkyl, aryl (meaning phenyl optionally substituted with halo, fluoro, alkyl, alkoxy, alkylthio, hydroxy, alkanoyl, nitro, amino, dialkylamino, trifluoromethyl, $C_{3-7}$ cycloalkyl or arylalkyl); $A_{100}$ is nitrogen (when the dotted substituted with a group selected independently from the list provided to define $R_{140}$ (when the dotted line is not a bond); and $R_{141}$ and $R_{142}$ are each independently hydrogen, halo, fluoro, nitro, amino, $C_{1-4}$ alkylamino, di($C_{1-4}$ alkyl)amino, trifluoromethyl, $C_{1-4}$ alkyl, $C_{1-4}$ alkoxy or a group of formula —$SO_2NHR_{143}$ (wherein $R_{143}$ is hydrogen, $C_{1-5}$ alkyl or arylmethylene);

(ix)

wherein $R_{150}$ is hydrogen, $C_{1-6}$ alkyl, a group of formula $Y_{60}$ wherein $Y_{60}$ is phenyl or 1- or 2-naphthyl (each optionally substituted by methyl, methoxy, hydroxy, bromo, chloro, fluoro, nitro, amino, diethylamino, methylthio or sulphydryl), a group of formula $C_{1-6}$ alkyl-$Y_{60}$- (wherein $Y_{60}$ is as defined above), a group of formula $Y_{61}$ (wherein $Y_{61}$ is a 5- or 6-membered ring or 8-, 9- or 10-membered bicyclic system containing one or more heteroatoms selected from nitrogen, oxygen and sulphur (including bun not limited to pyrrole, imidazole, thiophene, furan, pyridine, thiazole, indole, morpholine and isoquinoline)) optionally substituted by halo, fluoro, $C_{1-6}$ alkyl, $C_{1-6}$ alkyloxy or hydroxy; or a group of formula $C_{1-6}$alkyl-$Y_{61}$- (wherein $Y_{61}$ is as defined above);

(x)

wherein $A_{111}$ is oxygen, sulphur, imino or methylene; and if $A_{111}$ is oxygen, sulphur or imino, then $A_{110}$ is a group of formula —$CR_{160}R_{161}$— and if $A_{111}$ is methylene, then $A_{110}$ is either nitrogen or a group of formula —$CR_{160}R_{161}$— wherein $R_{160}$ and $R_{161}$ are each independently hydrogen, $C_{1-10}$ alkyl, $C_{3-10}$ alkenyl, $C_{3-10}$ alkynyl, $C_{3-8}$ cycloalkyl, $C_{4-10}$ cycloalkylalkyl, $C_{5-10}$ cycloalkylalkenyl, $C_{5-10}$ cycloalkyl alkynyl or aryl optionally substituted with one or two of halo, $C_{1-4}$ alkyl or $C_{1-4}$ alkoxy;

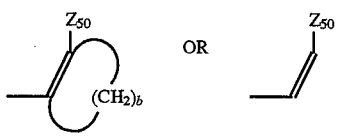

wherein b is 2, 3 or 4; or

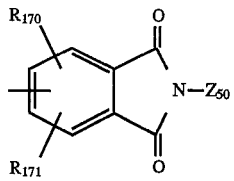

wherein $R_{171}$ is hydrogen, halo, fluoro, $C_{1-4}$ alkyl, $C_{1-4}$ alkoxy; and $R_{170}$ is hydrogen, halo, fluoro, $C_{1-4}$ alkyl, $C_{1-4}$ alkoxy, nitro, $C_{1-4}$ acyloxy, carboxy (optionally esterified), phenyl, furyl or a group of formula —$NHSO_2Me$, —$NHSO_2CF_3$, —$SO_2NH_2$ or —$CONHR_{172}$ (wherein $R_{172}$ is hydrogen, methyl or benzyl).

Suitably, when $X_{50}$ is a spacer group it is carbonyl, oxygen, sulphur, vinylene, difluorovinylene, monofluorovinylene, ethylene, perfluoroethylene, oxymethylene, thiomethylene, or a group of formula —$NR_{53}$—, —$CONR_{54}$—, —$NR_{54}CO$—, —$NHCR_{55}R_{56}$—, —$NR_{55}SO_2$—, —$SO_2NR_{55}$—, $CR_{55}R_{56}NH$—, —CH($OR_{57}$)—, —CH($OCOR_{58}$)—, or —$C(NR_{59})$— (where $R_{53}$ is hydrogen, $C_{2-4}$ acyl, $C_{1-6}$ alkyl, allyl, $C_{3-6}$ cycloalkyl, phenyl or benzyl, $R_{54}$ is hydrogen or $C_{1-4}$ alkyl, $R_{55}$ is hydrogen, $C_{1-5}$ alkyl, phenyl or benzyl, $R_{56}$ is hydrogen or $C_{1-14}$ alkyl, $R_{57}$ is hydrogen, $C_{1-8}$ alkyl, $C_{1-8}$ perfluoroalkyl, $C_{3-6}$ cycloalkyl, phenyl or benzyl, $R_{58}$ is hydrogen, $C_{1-6}$ alkyl, $C_{3-6}$ cycloalkyl, phenyl or benzyl, $R_{59}$ is a group of formula —$NR_{55}R_{56}$, —$OR_{56}$, —$NHC(O)NH_2$, —$NHC(S)NH_2$, —$NHSO_2$ benzyl or —$NHSO_2$phenyl (wherein $R_{55}$ and $R_{56}$ are as defined above);

Preferably $B_{50}$ is a group selected from the groups represented by xv to xxii below (wherein in each case $Z_{51}$ is a bond to $X_{50}$ and the other free valency is connected to the —$(CH_2)_r$—Het group);

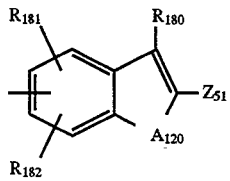

wherein $R_{180}$ is hydrogen, halo, (preferably bromo), fluoro, $C_{1-6}$ alkyl, $C_{2-6}$ alkenyl, $C_{1-6}$ fluoroalkyl, $C_{1-6}$ alkoxy, formyl, carboxy or a group of the formula —$COR_{183}$ (wherein $R_{183}$ represents $C_{1-6}$ alkyl, $C_{2-6}$ alkenyl, $C_{1-6}$ alkoxy or a group of formula —$NR_{184}R_{185}$, (wherein $R_{184}$ and $R_{185}$ are each independently hydrogen or $C_{1-4}$ alkyl or together form a saturated heterocyclic ring having 5 or 6 ring members and optionally comprising in the ring one oxygen atom)); $R_{181}$ and $R_{182}$ are each independently hydrogen, halo, fluoro, nitro, amino, $C_{1-4}$alkylamino, di($C_{1-4}$ alkyl) amino, trifluoromethyl, $C_{1-4}$ alkyl, $C_{1-4}$ alkoxy or a group of the formula —$SO_2NHR_{191}$ (wherein $R_{191}$ is hydrogen, $C_{1-5}$ alkyl, aryl or arylmethyl); and $A_{120}$ is oxygen, sulphur, or a group of formula —$NR_{186}$— {wherein $R_{186}$ is hydrogen or a group selected from $C_{1-6}$ alkyl, $C_{3-6}$ alkenyl, $C_{1-6}$ alkoxy, or a group of formula —$COR_{187}$ or —$SO_2R_{188}$ [wherein $R_{187}$ and $R_{188}$ are each $C_{1-6}$ alkyl, $C_{2-6}$ alkenyl, $C_{1-6}$ alkoxy or a group of formula —$NR_{189}R_{190}$ (wherein $R_{189}$ and $R_{190}$, which may be the same or different, each independently represent a hydrogen atom or a $C_{1-4}$ alkyl group or together complete a saturated heterocyclic ring having 5 or 6 ring members and optionally comprising in the ring one oxygen atom)]} and wherein preferably the free valency described above is located at the 5 position of the ring;

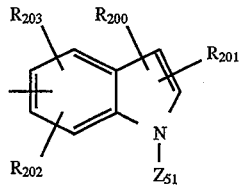

wherein $R_{200}$ and $R_{201}$ are each independently selected from the list provided to define $R_{180}$ above and $R_{202}$ and $R_{203}$ are each independently selected from the list provided to define $R_{181}$ above and wherein preferably the free valency described above located at the 5 position of the ring;

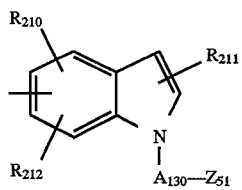

wherein $R_{210}$, $R_{211}$ and $R_{212}$ are each independently hydrogen, halo, fluoro, nitro, $C_{1-6}$ alkyl $C_{1-6}$ acyloxy, $C_{3-6}$ cycloalkyl, $C_{1-6}$ alkoxy, hydroxy-$C_{1-4}$ alkyl, $C_{1-4}$ alkylthio, $C_{1-4}$ alkylsulphinyl, $C_{1-4}$alkylsulphonyl, trifluoromethyl, aryl, furyl or a group of formula —$NHSO_2R_{213}$, —$SO_2NHR_{213}$ or —$NR_{213}R_{214}$ wherein $R_{213}$ and $R_{214}$ are each independently hydrogen, $C_{1-6}$ alkyl, benzyl or phenyl or, when $R_{210}$ and $R_{211}$ are bonded to adjacent carbon atoms, they may together complete a fused aromatic ring; and $A_{130}$ is carbonyl, methylene, or a group of formula —CH($CO_2C_{1-4}$ alkyl)—, —CH($CO_2H$)—, —CH(CN)—, —CH(tetrazolyl)— or —CH($CONHSO_2R_{215}$)— wherein $R_{215}$ is aryl, heteroaryl, $C_{3-7}$ cycloalkyl or $C_{1-4}$ alkyl (optionally substituted with aryl, heteroaryl, hydroxy, sulphydryl, $C_{1-4}$ alkyl, $C_{1-4}$ alkoxy, $C_{1-4}$ alkylthio, methyl, halo, fluoro, nitro, carboxy, carboxy ($C_{1-4}$ alkyl), amino, ii ($C_{1-4}$ alkyl)amino, or a group of formula —$PO_3H$ or —$PO(OH)[O$—($C_{1-4}$ alkyl)] and wherein preferably the free valency described above is located at the 5 position of the ring;

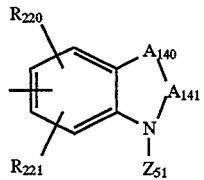

wherein $R_{220}$ and $R_{221}$ are each hydrogen, halo, fluoro, nitro, amino, $C_{1-4}$alkylamino, di($C_{1-4}$ alkyl)amino, trifluoromethyl, $C_{1-4}$ alkyl, $C_{1-4}$ alkoxy or a group of the formula —$SO_2NHR_{228}$ (wherein $R_{228}$ is hydrogen, $C_{1-5}$ alkyl, aryl or arylmethyl); and —$A_{140}$—$A_{141}$— are a group of the formula —N=$CR_{222}$—, —$CR_{222}$=$CR_{223}$— —$CHR_{222}$—$CHR_{223}$—;

wherein $R_{222}$ and $R_{223}$ are each independently hydrogen, halo fluoro, alkyl, haloalkyl; $C_{3-7}$ cycloalkyl or arylalkyl (wherein aryl is phenyl optionally substituted with halo, fluoro, alkyl, alkoxy, alkylthio, hydroxy, alkanoyl, nitro, amino, trifluoromethyl, alkylamino or dialkylamino) or a group of formula —$COR_{224}$ (wherein $R_{224}$ is hydrogen, $C_{1-6}$ alkyl, $C_{3-6}$ cycloalkyl or a group of formula —$OR_{225}$ or —$NR_{226}R_{227}$ wherein $R_{225}$ is hydrogen, $C_{1-6}$ alkyl, $C_{3-6}$ cycloalkyl, aryl, arylalkyl or a 5 to 7 membered carbocyclic ring which may have another 5 to 7 membered carbocyclic ring fused thereto and $R_{226}$ and $R_{222}$ are each independently hydrogen, $C_{1-4}$ alkyl, phenyl, benzyl, α-methyl benzyl or together form a $C_{3-4}$ cyclic group optionally containing nitrogen and/or oxygen in the ring) and wherein preferably the free valency described above is located at the 5 position of the ring;

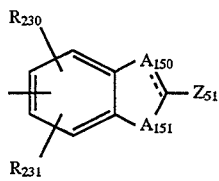  (xix)

wherein $R_{230}$ and $R_{231}$ are each independently hydrogen, halo, fluoro, nitro, amino, $C_{1-4}$ alkylamino, di($C_{1-4}$ alkyl) amino, trifluoromethyl, $C_{1-4}$ alkyl, $C_{1-4}$ alkoxy or a group of formula —$SO_2NHR_{234}$ (wherein $R_{234}$ is hydrogen, $C_{1-5}$ alkyl, aryl or arylmethyl); $A_{150}$ and $A_{151}$ are each independently oxygen, sulphur or a group of the formula —$NR_{232}$— or —$CR_{232}R_{233}$— wherein $R_{232}$ and $R_{233}$ are each independently hydrogen, $C_{1-6}$ alkyl, $C_{3-6}$ cycloalkyl, phenyl or benzyl and wherein preferably the free valency described above is located at the 5 position of the ring;

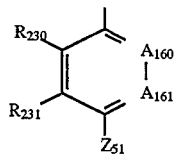  (xx)

wherein —$A_{160}$—$A_{161}$— is a group of formula =$C(R_{239})$—N= or =N—$C(R_{232})$= and wherein $R_{230}$ $R_{231}$ and $R_{232}$ are each independently hydrogen, halo, fluoro, nitro, amino, $C_{1-4}$ alkyl, $C_4$alkylamino, di($C_{1-4}$ alkyl)amino, $C_{1-4}$ alkoxy, trifluoromethyl, or a group of formula —$SO_2NHR_{233}$ (wherein $R_{233}$ is hydrogen, $C_{1-5}$ alkyl, aryl or arylmethyl);

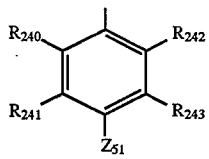  (xxi)

wherein $R_{240}$ to $R_{243}$ are each independently hydrogen, halo, fluoro, $C_{1-6}$ alkyl, $C_{1-6}$ perfluoroalkyl, $C_{1-6}$ alkoxy or $C_{1-6}$ alkoxyalkyl; or

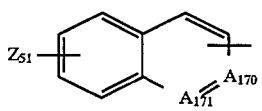  (xxii)

wherein —$A_{170}$=$A_{171}$— is a group of formula —$C(R_{250})$=N— or —$C(R_{251})$=$C(R_{252})$— wherein $R_{250}$ is hydrogen or $C_{1-7}$ alkyl and $R_{251}$ and $R_{252}$ are each hydrogen, halo, fluoro, $C_{1-7}$ alkyl, $C_{1-7}$ alkoxy, $C_{2-7}$ alkenyloxy, phenoxy, benzyloxy, trifluoromethyl or a group of formula —$S(O)_f$—$R_{253}$ (wherein f is 0 or an integer from 1 to 2 and $R_{253}$ is hydrogen or $C_{1-7}$ alkyl).

Preferably, r is 1.

Preferably Het is a group of any of the following formulae, in which in each case the symbols are as defined in the corresponding patent publication(s) identified in brackets. Preferred and/or specific heterocycles are as identified in said corresponding patent publication(s):

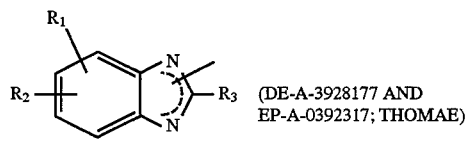 (DE-A-3928177 AND EP-A-0392317; THOMAE)

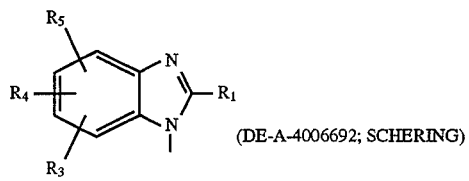 (DE-A-4006692; SCHERING)

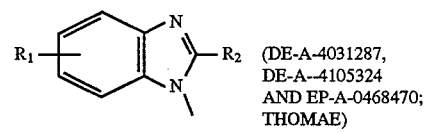 (DE-A-4031287, DE-A-4105324 AND EP-A-0468470; THOMAE)

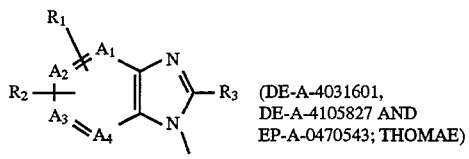 (DE-A-4031601, DE-A-4105827 AND EP-A-0470543; THOMAE)

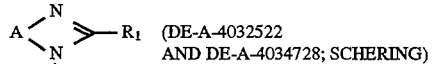 (DE-A-4032522 AND DE-A-4034728; SCHERING)

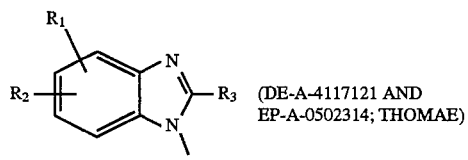 (DE-A-4117121 AND EP-A-0502314; THOMAE)

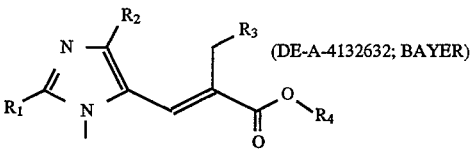 (DE-A-4132632; BAYER)

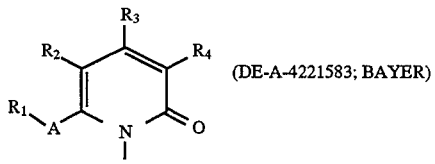 (DE-A-4221583; BAYER)

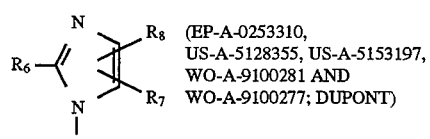 (EP-A-0253310, US-A-5128355, US-A-5153197, WO-A-9100281 AND WO-A-9100277; DUPONT)

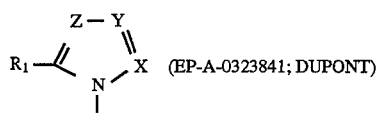 (EP-A-0323841; DUPONT)

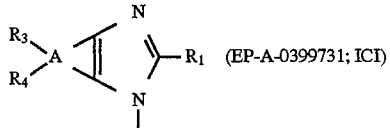 (EP-A-0399731; ICI)
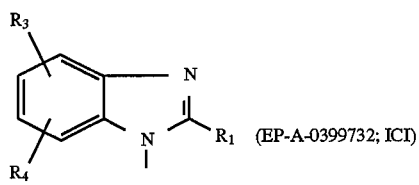 (EP-A-0399732; ICI)
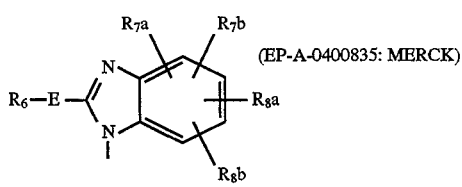 (EP-A-0400835; MERCK)
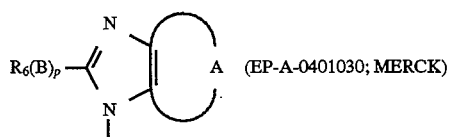 (EP-A-0401030; MERCK)
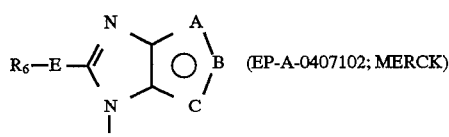 (EP-A-0407102; MERCK)
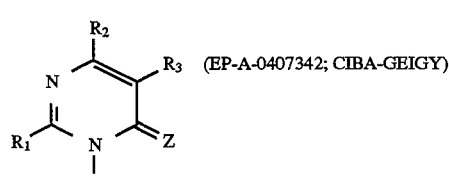 (EP-A-0407342; CIBA-GEIGY)
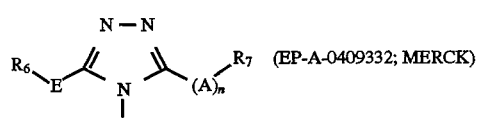 (EP-A-0409332; MERCK)
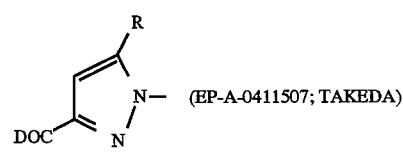 (EP-A-0411507; TAKEDA)
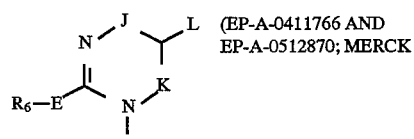 (EP-A-0411766 AND EP-A-0512870; MERCK)
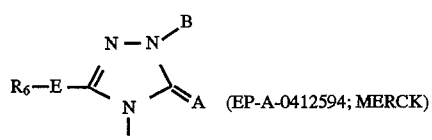 (EP-A-0412594; MERCK)
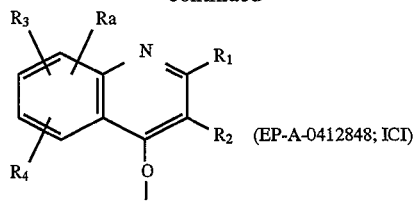 (EP-A-0412848; ICI)
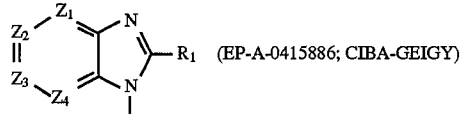 (EP-A-0415886; CIBA-GEIGY)
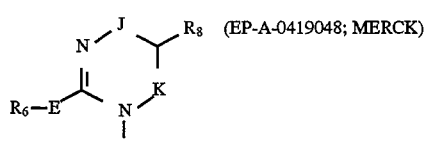 (EP-A-0419048; MERCK)
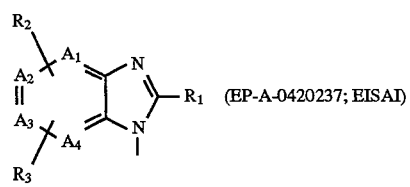 (EP-A-0420237; EISAI)
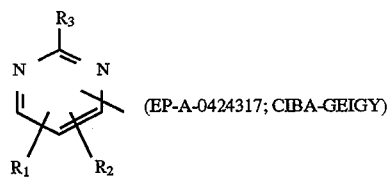 (EP-A-0424317; CIBA-GEIGY)
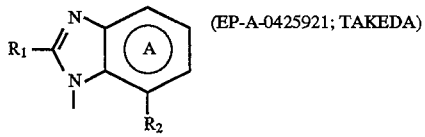 (EP-A-0425921; TAKEDA)
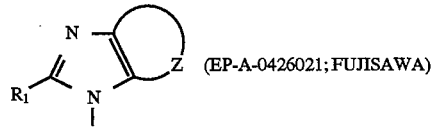 (EP-A-0426021; FUJISAWA)
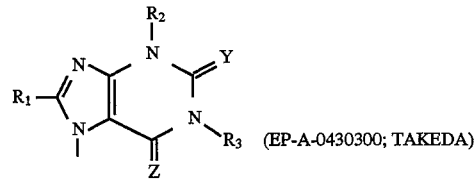 (EP-A-0430300; TAKEDA)
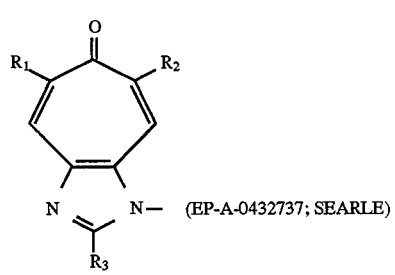 (EP-A-0432737; SEARLE)

-continued
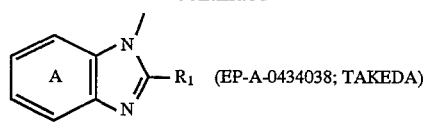 (EP-A-0434038; TAKEDA)
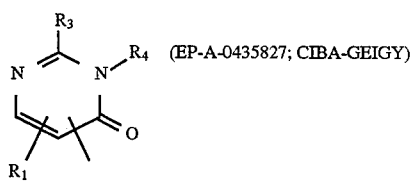 (EP-A-0435827; CIBA-GEIGY)
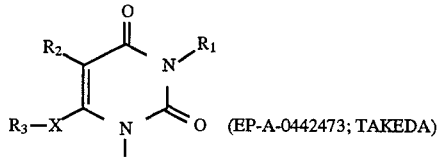 (EP-A-0442473; TAKEDA)
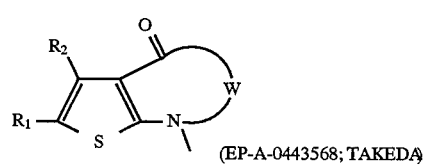 (EP-A-0443568; TAKEDA)
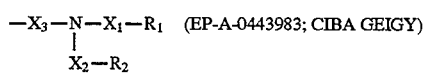 (EP-A-0443983; CIBA GEIGY)
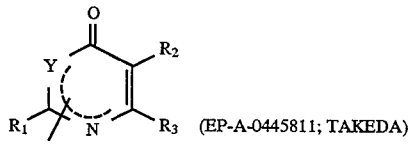 (EP-A-0445811; TAKEDA)
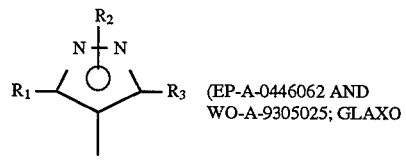 (EP-A-0446062 AND WO-A-9305025; GLAXO)
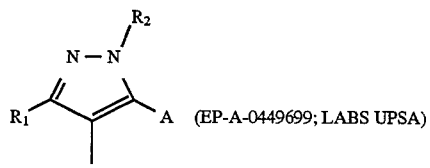 (EP-A-0449699; LABS UPSA)
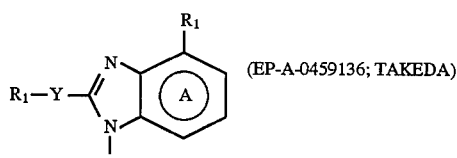 (EP-A-0459136; TAKEDA)
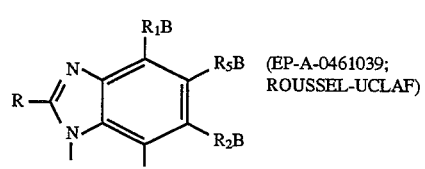 (EP-A-0461039; ROUSSEL-UCLAF)
-continued
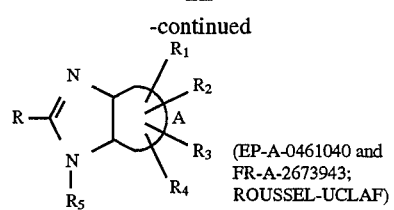 (EP-A-0461040 and FR-A-2673943; ROUSSEL-UCLAF)
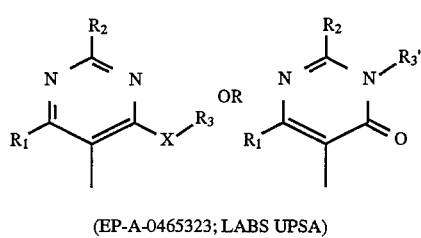 (EP-A-0465323; LABS UPSA)
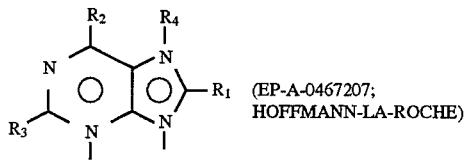 (EP-A-0467207; HOFFMANN-LA-ROCHE)
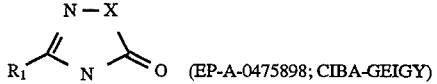 (EP-A-0475898; CIBA-GEIGY)
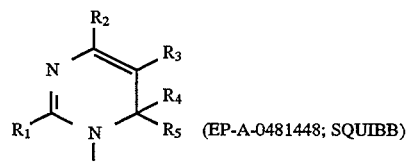 (EP-A-0481448; SQUIBB)
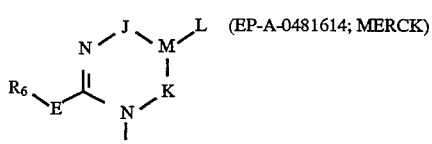 (EP-A-0481614; MERCK)
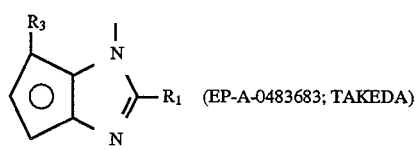 (EP-A-0483683; TAKEDA)
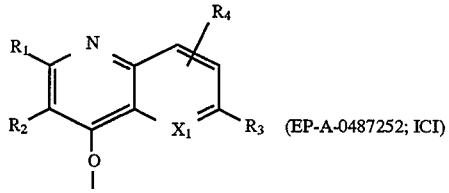 (EP-A-0487252; ICI)
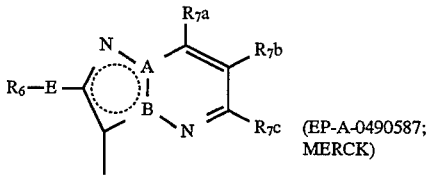 (EP-A-0490587; MERCK)

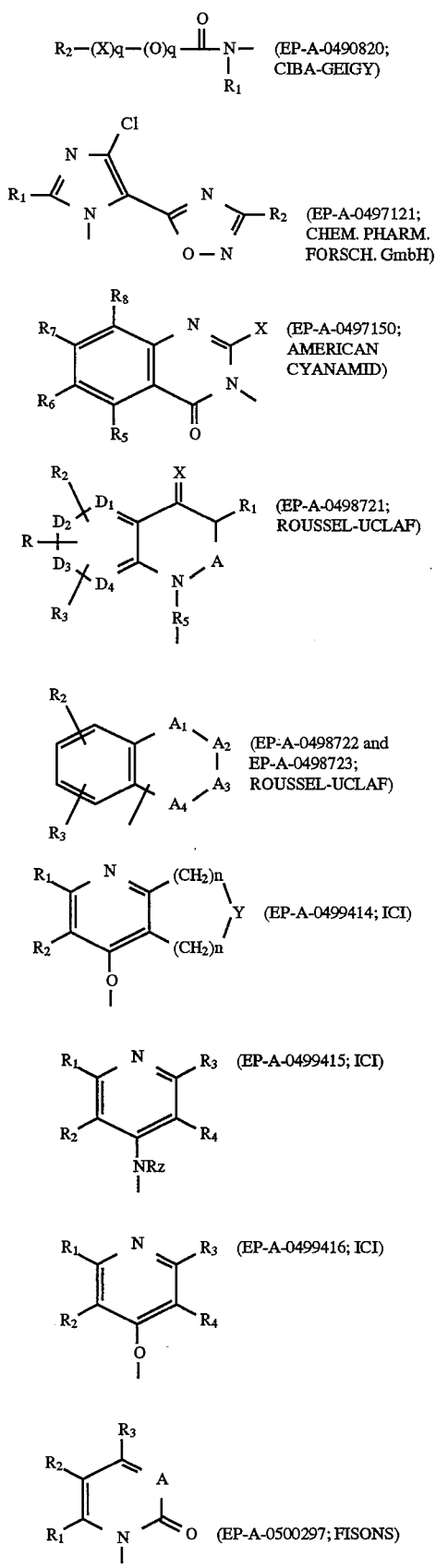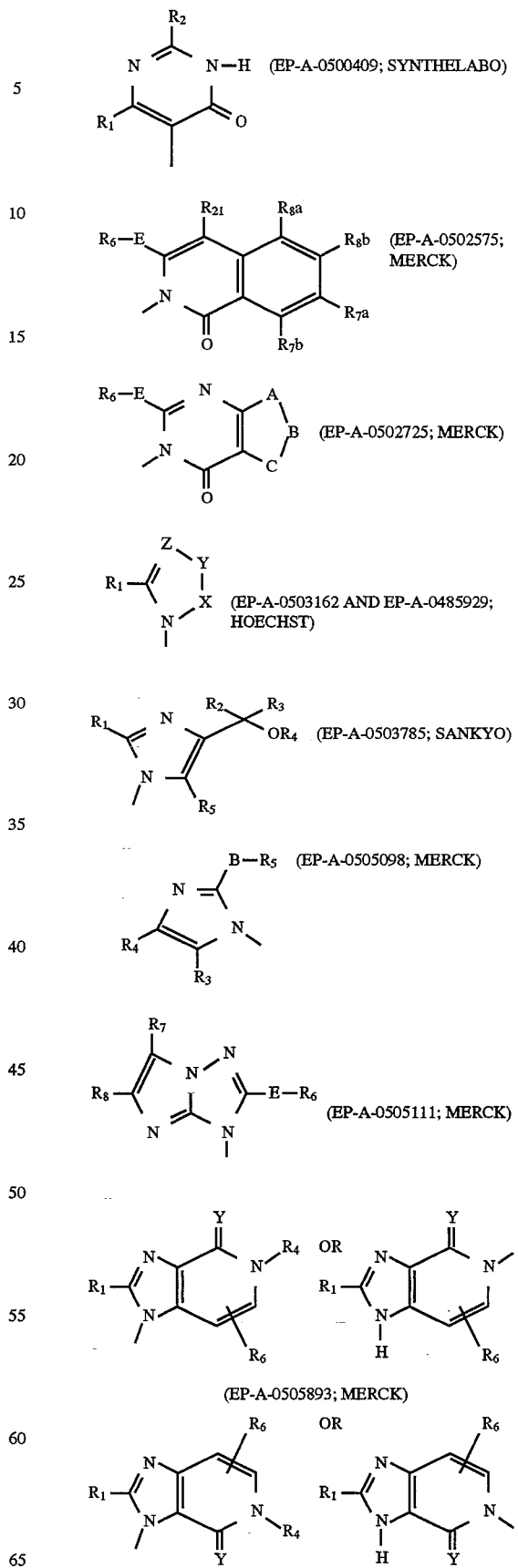

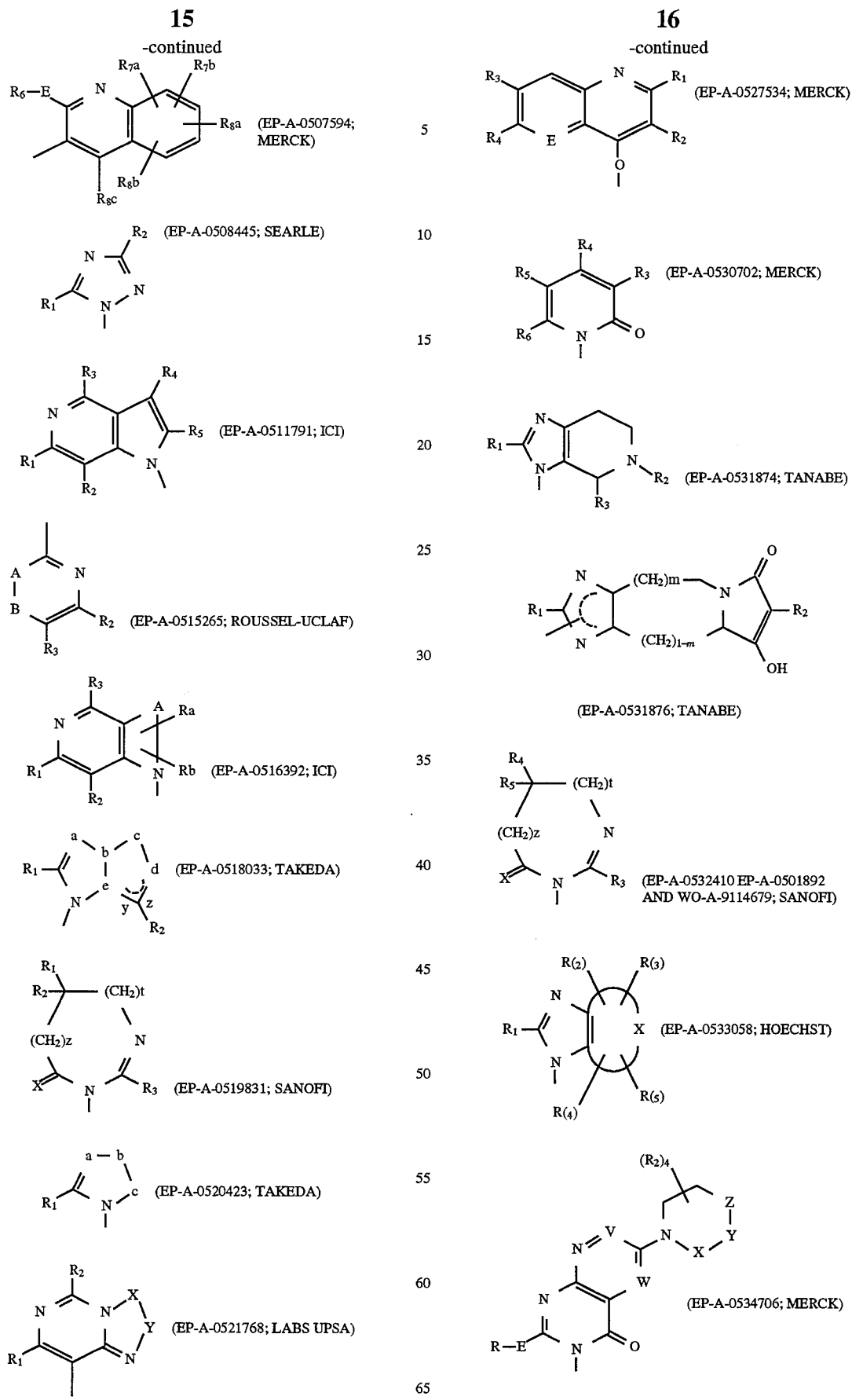

-continued
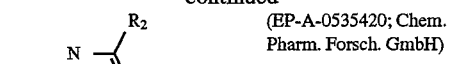
(EP-A-0535420; Chem. Pharm. Forsch. GmbH)
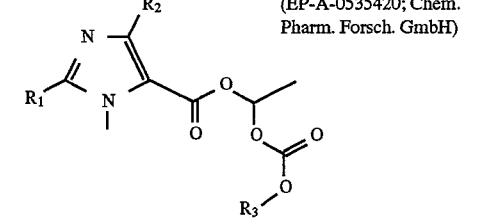
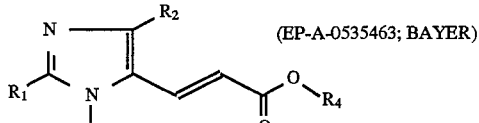
(EP-A-0535463; BAYER)
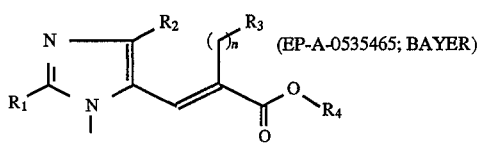
(EP-A-0535465; BAYER)
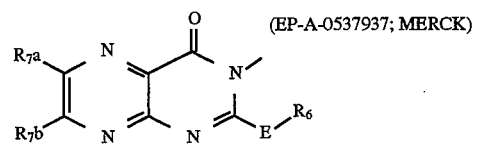
(EP-A-0537937; MERCK)
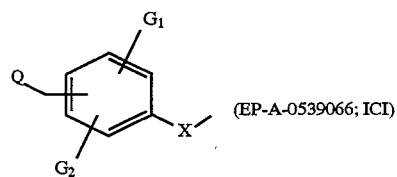
(EP-A-0539066; ICI)
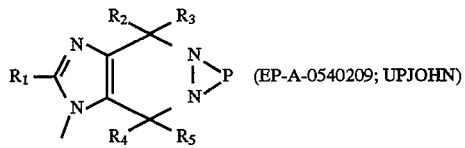
(EP-A-0540209; UPJOHN)
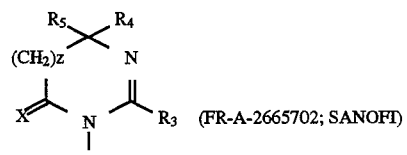
(FR-A-2665702; SANOFI)
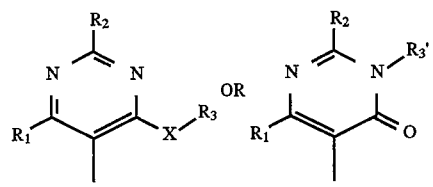
(FR-A-2669928 AND EP-A-0465323; LABS UPSA)
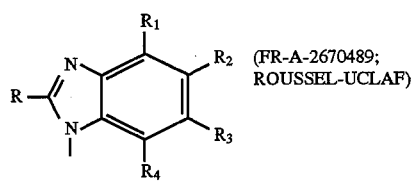
(FR-A-2670489; ROUSSEL-UCLAF)
-continued
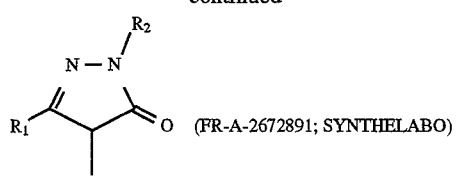
(FR-A-2672891; SYNTHELABO)
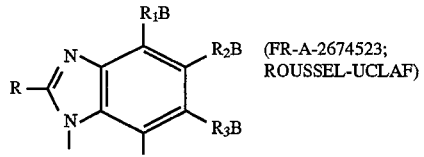
(FR-A-2674523; ROUSSEL-UCLAF)
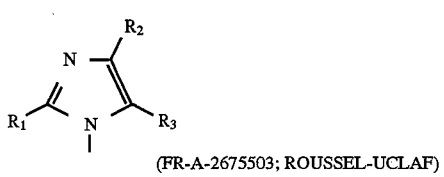
(FR-A-2675503; ROUSSEL-UCLAF)
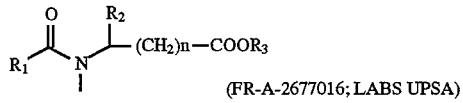
(FR-A-2677016; LABS UPSA)
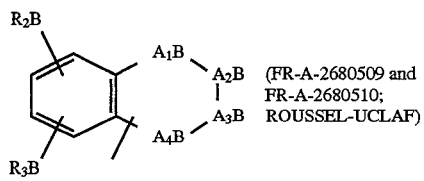
(FR-A-2680509 and FR-A-2680510; ROUSSEL-UCLAF)
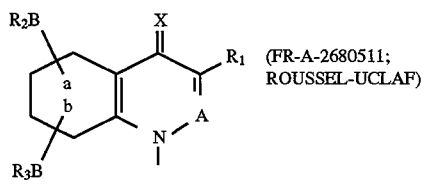
(FR-A-2680511; ROUSSEL-UCLAF)
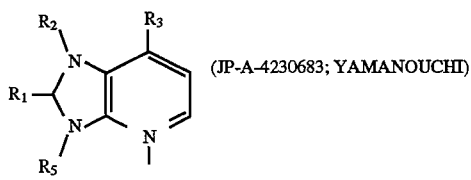
(JP-A-4230683; YAMANOUCHI)
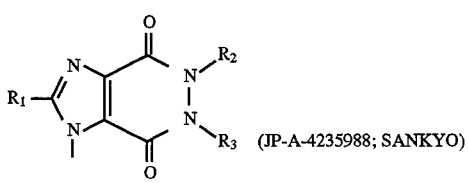
(JP-A-4235988; SANKYO)
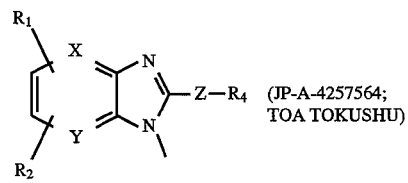
(JP-A-4257564; TOA TOKUSHU)

-continued (JP-A-5017480; FUJISAWA)

(US-A-4880804; DUPONT)

(US-A-4916129; DUPONT)

(US5043349; DUPONT)

(US-A-5087634; SEARLE)

(US-A-5091390; DUPONT)

(US-A-5093346; DUPONT)

(US-A-5102880 EP-A-0503838 AND EP-A-0400974; MERCK)

(US-A-5124335; MERCK)

-continued (US-A-5149699; AMERICAN HOME PRODUCTS)

(US-A-5153347; SQUIBB)

(US-A-5162340; MERCK)

(US-A-5166206; MERCK)

(US-A-5177095; MERCK)

(US-A-5177097; SQUIBB)

(US-A-5182288; ORTHO PHARM.)

(US-A-5208235; SQUIBB)

(WO-A-8908653; SEARLE)

-continued
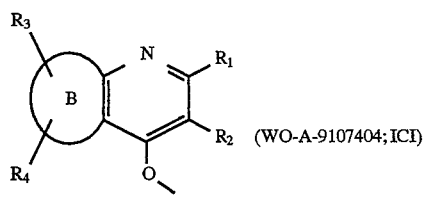 (WO-A-9107404; ICI)
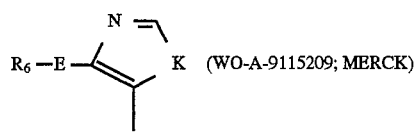 (WO-A-9115209; MERCK)
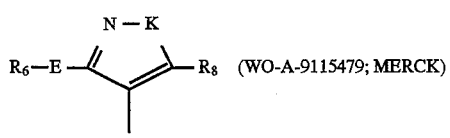 (WO-A-9115479; MERCK)
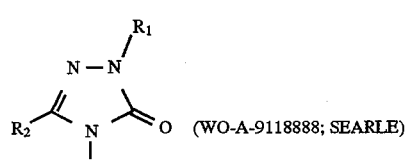 (WO-A-9118888; SEARLE)
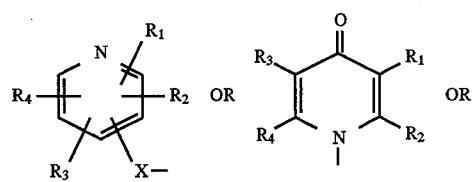 (WO-A-9119697; MEIJI SEIKA)
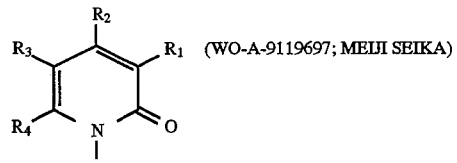 (WO-A-9119715; SEARLE)
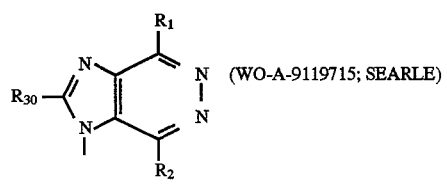 (WO-A-9200977; DUPONT)
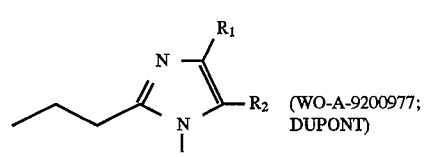 (WO-A-9204335 AND WO-A-9205161; SEARLE)
-continued
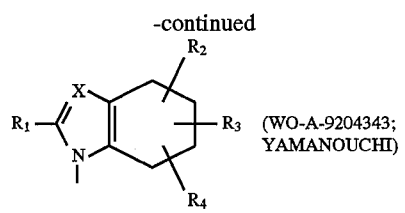 (WO-A-9204343; YAMANOUCHI)
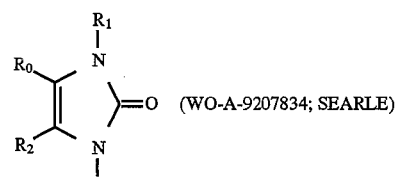 (WO-A-9207834; SEARLE)
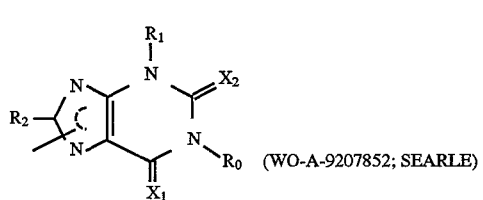 (WO-A-9207852; SEARLE)
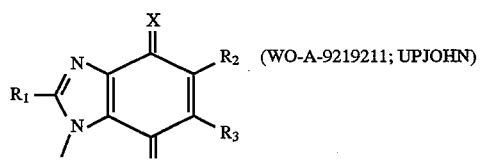 (WO-A-9219211; UPJOHN)
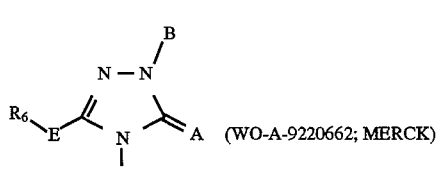 (WO-A-9220662; MERCK)
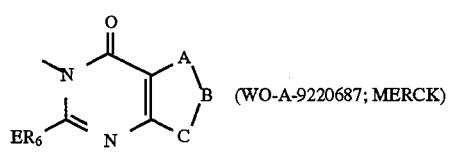 (WO-A-9220687; MERCK)
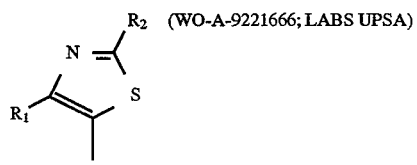 (WO-A-9221666; LABS UPSA)
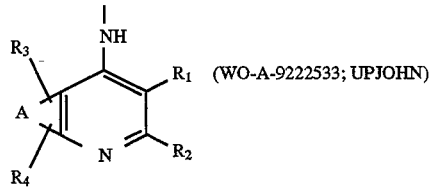 (WO-A-9222533; UPJOHN)
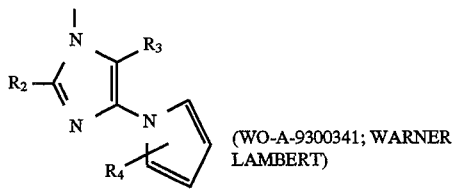 (WO-A-9300341; WARNER LAMBERT)

-continued

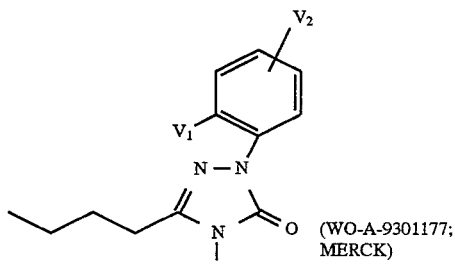 (WO-A-9301177; MERCK)

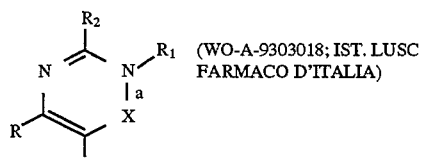 (WO-A-9303018; IST. LUSC FARMACO D'ITALIA)

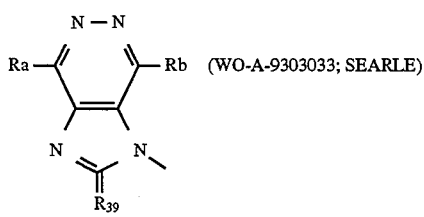 (WO-A-9303033; SEARLE)

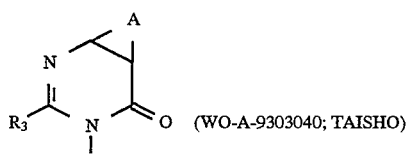 (WO-A-9303040; TAISHO)

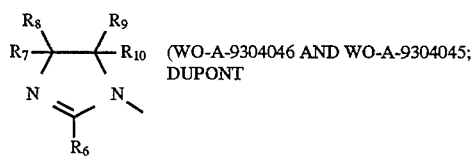 (WO-A-9304046 AND WO-A-9304045; DUPONT

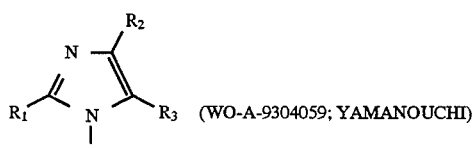 (WO-A-9304059; YAMANOUCHI)

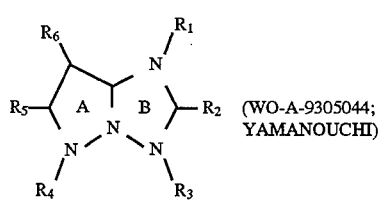 (WO-A-9305044; YAMANOUCHI)

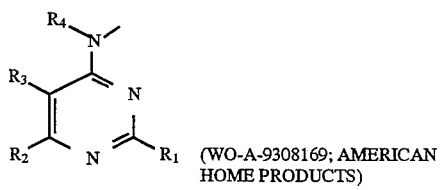 (WO-A-9308169; AMERICAN HOME PRODUCTS)

-continued

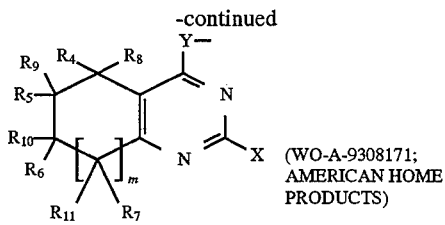 (WO-A-9308171; AMERICAN HOME PRODUCTS)

Suitably, Het comprises a heterocyclic group, that is a group comprising a closed organic ring system which ring system contains one or more oxygen, nitrogen or sulphur atoms. Preferably, Het comprises a stable 5- to 7-membered monocyclic or 7- to 10-membered bicyclic heterocyclic ring which is either saturated or unsaturated, and which consists of carbon atoms and up to five, preferably up to three nitrogen, oxygen and/or sulphur atoms (wherein any nitrogen atom may optionally be quaternized), and including any bicyclic group in which any of the above-defined mono-heterocyclic rings is fused to a benzene ring, and wherein the ring is optionally substituted. Such heterocyclic groups include (but are not limited to): thienyl, furyl, pyranyl, chromenyl, xanthenyl, pyrrolyl, 2H-pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, quinolizinyl, quinolyl, phthalazinyl, naphthyridinyl, quinoxalinyl, quinazolinyl, cinnolinyl, pteridinyl, isothiazolyl, isoxazolyl, furazanyl, piperazinyl, pyrrolidinyl, oxazolyl, triazolyl and tetrazolyl and any isomers thereof and, where the context permits, dihydro, tetrahydro, mono-one, di-one and tri-one derivatives thereof. Heterocyclic groups of the present invention also include fused rings based on any combination of up to three of the foregoing and/or benzene or naphthalene. Preferred heterocycles are based on benzimidazole and imidazopyridine.

Groups of formula i, ii iii, iv, v, vi, vii, viii, ix, x, xi and xii are disclosed in a) EP-A-0513533 (Bayer; b) EP-A-0480204 (Fujisawa); c) U.S. Pat. No. 5,124,335 (Merck; d) EP-A-0512676 (Merck); e) EP-A-0512675 (Merck; f) WO-A-9112001 (Merck); g) WO-A-9215577 (Searle); h) EP-A-0501269 (Squibb); i) WO-A-9206081 (Warner Lambert); j) U.S. Pat. No. 5,191,086 (Squibb); k) DE-A-4006693 (Schering); and l) EP-A-0253310 (Du Pont) respectively, and preferred groups are as described in these publications.

Groups of formula xv, xvi, xvii, xviii, xix, xx, xxi and xxii are disclosed in m) WO-A-9209600, EP-A-0514193, EP-A-0514192, EP-A-0430709, EP-A-0514198, EP-A-0514197, EP-A-0514216, EP-A-0505954 and EP-A-0514217 (Glaxo); n) EP-A-0429257 (Glaxo); o) EP-A-0517357 (Merck); p) EP-A-0488532 (Squibb); q) U.S. Pat. No. 5,190,942 (Squibb); r) EP-A-0508393 (Searle); s) EP-A-0400974 (Merck); and t) EP-A-0528762 (Ciba Geigy) respectively, and preferred groups are as described in these publications.

Preferably Het is a group of any one of the formulae xxv, xxvi, xxvii or xxviii below:

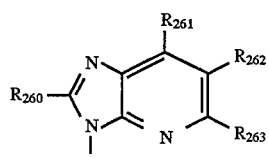 (xxv)

wherein $R_{260}$ is hydrogen or $C_{1-4}$ alkyl and $R_{261}$, $R_{262}$ and $R_{263}$ are each independently hydrogen, $C_{1-4}$ alkyl, nitro, fluoro, chloro, bromo, cyano, formyl, or a group of the formula —SO$_n$R$_{264}$, —SO$_2$NR$_{265}$R$_{266}$ or —COR$_{267}$ (wherein R$_{264}$, R$_{265}$ and R$_{266}$ are each independently hydrogen or C$_{1-4}$ alkyl, n is 1 or 2 and R$_{267}$ is C$_{1-4}$ alkyl or a group of formula —OR$_{268}$ or —NR$_{269}$R$_{270}$ wherein R$_{268}$, R$_{269}$ and R$_{270}$ are each independently hydrogen or C$_{1-8}$ alkyl);

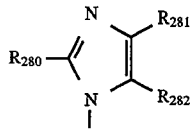

(xxvi)

wherein R$_{280}$ is hydrogen or C$_{1-6}$ alkyl; R$_{281}$ is hydrogen, chloro, fluorinated (preferably perfluorinated) C$_{1-2}$ alkyl (preferably trifluoromethyl or pentafluoroethyl), aryl C$_{1-4}$ alkyl, C$_{1-4}$ alkylsulphinyl, C$_{1-4}$ alkylsulphonyl, C$_{1-4}$ alkylthio, arylsulphinyl, arylsulphonyl, arylthio, arylmethylsulphinyl, arylmethylsulphonyl or arylmethylthio (wherein "aryl" denotes phenyl or 1- or 2-naphthyl each optionally substituted by C$_{1-4}$ alkyl, C$_{1-4}$ alkoxy or fluoro, chloro or bromo); and R$_{282}$ is hydroxymethyl, formyl, carboxy, C$_{2-4}$ alkoxymethyl, C$_{2-4}$ alkoxycarbonyl or carboxymethyl;

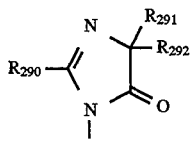

(xxvii)

wherein R$_{290}$ is hydrogen or C$_{1-6}$ alkyl and either R$_{291}$ and R$_{292}$ are each independently hydrogen, C$_{1-4}$ alkyl or phenyl (optionally substituted with C$_{1-4}$ alkyl, C$_{1-4}$ alkoxy, fluoro, chloro or bromo) or R$_{291}$ and R$_{292}$ together with the carbon atom to which they are attached form a C$_{3-6}$ spirocycloalkyl ring; or

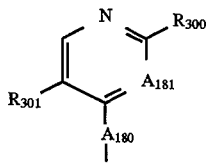

(xxviii)

wherein A$_{180}$ is oxygen, sulphur or a group of the formula —NR$_{302}$— wherein R$_{302}$ is C$_{1-6}$ alkyl, A$_{181}$ is nitrogen or methine, R$_{300}$ is hydrogen, C$_{1-4}$ alkyl, C$_{1-4}$ alkylthio or aryl C$_{1-4}$ alkyl (wherein "aryl" denotes phenyl, optionally substituted by C$_{1-4}$ alkyl, C$_{1-4}$ alkoxy, or fluoro, chloro or bromo) and R$_{301}$ is hydrogen, carboxy, carbamoyl or a group of formula —C(O)NR$_{303}$R$_{304}$ (wherein R$_{303}$ and R$_{304}$ are each independently C$_{1-4}$ alkyl or hydroxy-substituted C$_{1-4}$ alkyl or C$_{1-4}$ alkyl).

Preferably in groups of formula xxv, R$_{260}$ is ethyl, R$_{262}$ is hydrogen and R$_{261}$ and R$_{263}$ are both methyl.

Preferably in groups of formula xxvi, R$_{280}$ is butyl and R$_{281}$ is chloro.

Preferably in groups of formula xxvii, R$_{290}$ is butyl and R$_{291}$ and R$_{292}$ together with the carbon atom to which they are attached form a spirocyclopentane ring.

Preferably in groups of formula xxviii, A$_{180}$ is a group of formula —NBu—, R$_{300}$ is hydrogen, and R$_{301}$ is carboxy.

In preferred compounds of formula I, A$_{50}$ is a group of formula (iii) above, X$_{50}$ is a bond, B$_{50}$ is a group of formula (xxi) above and Het is a heterocyclic ring as defined above.

Preferred compounds of formula are compounds of formula II

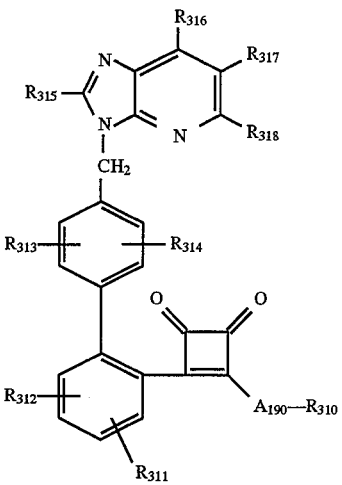

II wherein

R$_{310}$ is hydrogen or C$_{1-4}$ alkyl; A$_{190}$ is oxygen, sulphur or a group of the formula —NR$_{319}$— wherein R$_{319}$ is hydrogen or C$_{1-4}$ alkyl;

R$_{311}$, R$_{312}$, R$_{313}$ and R$_{314}$ are each independently hydrogen, fluoro, chloro, bromo, C$_{1-4}$ alkyl, C$_{1-4}$ alkoxy, nitro, cyano, carboxy, C$_{2-4}$ alkoxycarbonyl, C$_{1-4}$ alkylthio, C$_{1-4}$ alkylsulphinyl, C$_{1-4}$ alkylsulphonyl, phenyl (optionally substituted by C$_{1-4}$ alkyl, C$_{1-4}$ alkoxy, fluoro, chloro or bromo), C$_{1-4}$ alkylsulphonylamino or C$_{1-6}$alkylaminosulphonyl; R$_{315}$ is hydrogen or C$_{1-4}$ alkyl; and R$_{316}$, R$_{317}$ and R$_{318}$ are each independently hydrogen, C$_{1-4}$ alkyl, nitro, fluoro, chloro, bromo, cyano, formyl or a group of the formula —SO$_g$R$_{320}$, —SO$_2$NR$_{321}$R$_{322}$ or —COR$_{323}$ (wherein R$_{320}$, R$_{321}$, R$_{322}$ are each independently hydrogen or C$_{1-4}$ alkyl, g is 1 or 2 and R$_{323}$ is C$_{1-4}$ alkyl or a group of the formula —OR$_{324}$ or —NR$_{325}$R$_{326}$ wherein R$_{324}$, R$_{325}$ and R$_{326}$ are each independently hydrogen or C$_{1-4}$ alkyl);

and pharmaceutically acceptable salts thereof.

Particularly preferred compounds of formula I are represented by formula III

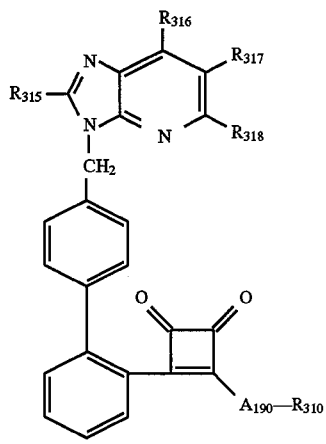

III wherein A$_{190}$, R$_{310}$, R$_{315}$, R$_{316}$, R$_{317}$ and R$_{318}$ are each as defined above;

and pharmaceutically acceptable salts thereof.

Especially preferred compounds of formula I are represented by formula IV:

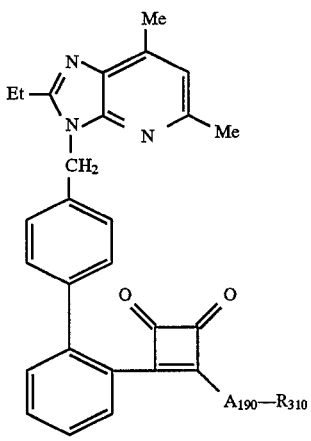

in which $A_{190}$ and $R_{310}$ are as defined above;
and pharmaceutically acceptable salts thereof.

In preferred compounds of formulae II, III and IV, $A_{190}$ is oxygen and $R_{310}$ is hydrogen.

Further preferred compounds of formula I are represented by formula V

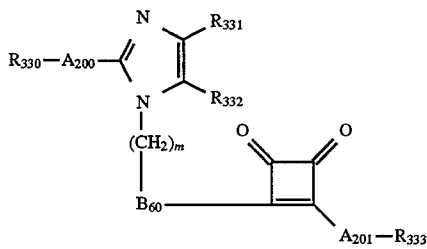

and pharmaceutically acceptable salts thereof;

wherein $R_{330}$ is $C_{2-10}$ alkyl, $C_{3-10}$ alkenyl or a group of formula —$(CH_2)_hC_{3-6}$cycloalkyl, or —$(CH_2)_h$phenyl, wherein h is 0 or an integer from 1 to 8 (optionally substituted by up to three of $C_{1-6}$ alkyl, nitro, cyano, halo, fluoro, $C_{1-3}$ perfluoroalkyl, $C_{1-3}$ perfluoroalkylsulphonyl, $C_{1-6}$alkylsulphonyl, $C_{1-6}$ alkylthio, hydroxy, $C_{1-6}$ alkoxy, or a group of formula —$NR_{334}R_{335}$, —$CO_2R_{334}$, —$CONR_{334}R_{335}$, —$PO(OR_{334})_2$, —$NR_{334}CHO$, —$NR_{334}O(C_{1-6}$ alkyl) or —$NR_{334}COR_{336}$ (wherein $R_{334}$ and $R_{335}$ are each independently hydrogen or $C_{1-4}$ alkyl and $R_{336}$ is $C_{1-3}$ perfluoroalkyl);

$A_{200}$ is a bond, sulphur or oxygen; $R_{331}$ is hydrogen, halo, fluoro, formyl, nitro, $C_{1-3}$ perfluoroalkyl, cyano $C_{1-6}$ alkyl, phenyl, hydroxymethyl, or a group of formula —$CO_2R_{338}$, —$CONR_{338}R_{339}$ or —$NR_{338}R_{339}$ (wherein $R_{338}$ and $R_{239}$ are each independently hydrogen or $C_{1-4}$ alkyl);

m is 0 or an integer from 1 to 4;

$B_{60}$ is 1,4-phenylene, 1,4-naphthylene, or 2,5-pyridylene, optionally substituted with one or more of halo, fluoro, $C_{1-4}$ alkyl, nitro, hydroxy, $C_{1-4}$ alkoxy $C_{1-4}$ alkylsulphonyl, $C_{1-3}$ perfluoroalkyl, nitrile, or a group of formula —$SO_2NHR_{388}$, —$NHSO_2R_{338}$ or —$CONR_{338}R_{339}$ (wherein $R_{338}$ and $R_{339}$ are each as defined above;

$A_{201}$ is oxygen, sulphur, or a group of formula —$NR_{337}$— (wherein $R_{337}$ is hydrogen or $C_{1-4}$ alkyl);

$R_{333}$ is hydrogen or $C_{1-4}$ alkyl;

and $R_{332}$ is a group selected from the groups represented by xxx to xxxiii below:

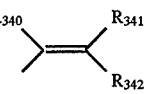

(xxx)

wherein $R_{340}$ and $R_{341}$ are each independently hydrogen, $C_{1-6}$ alkyl, $C_{3-6}$ cycloalkyl or a group of formula phenyl—Y—$_{70}$—, biphenyl—$Y_{70}$—, naphthyl—$Y_{70}$—, thienyl—$Y_{70}$—, furyl—$Y_{70}$—, pyridyl —$Y_{70}$—, pyrazolyl—$Y_{70}$—, imidazolyl—$Y_{70}$—, pyrrolyl —$Y_{70}$—, triazolyl—$Y_{70}$—, oxazolyl—$Y_{70}$—, isoxazolyl—$Y_{70}$—, thiazolyl—$Y_{70}$—, or tetrazolyl —$Y_{70}$—, with each aryl or heteroaryl group optionally substituted by hydroxy, nitro, $C_{1-3}$ perfluoroalkyl, $C_{1-3}$ perfluoroalkylsulphonyl, $C_{1-6}$ alkylthio, $C_{1-6}$ alkylsulphonyl, $C_{1-6}$ alkyl, $C_{1-6}$ alkoxy, halo, fluoro, or a group of formula —$NR_{343}R_{344}$, —$CO_2R_{343}$, —$SO_2NHR_{343}$, —$SO_3H$, —$CONR_{343}R_{344}$, —$NR_{343}CHO$, —$NR_{343}CO(C_{1-3}$perfluoroalkyl), or —$NR_{343}CO(C_{1-6}$ alkyl) wherein $R_{343}$ and $R_{344}$ are each independently hydrogen or $C_{1-6}$ alkyl ; $Y_{70}$ is a bond, oxygen, sulphur or $C_{1-6}$ alkylene optionally substituted by phenyl or benzyl, (wherein each phenyl or benzyl group is optionally substituted by halo, nitro, trifluoromethyl, $C_{1-6}$ alkyl, $C_{1-6}$ alkoxy, cyano or a group of formula —$CO_2R_{345}$ wherein $R_{345}$ is hydrogen or $C_{1-4}$ alkyl); $R_{342}$ is —$Y_{71}$—$COOR_{346}$ (wherein $R_{366}$ is hydrogen $C_{1-6}$ alkyl, or 2-di($C_{1-6}$ alkyl)-amino-2-oxyethyl); —$Y_{71}$ $CONR_{347}R_{348}$ (wherein $R_{347}$ and $R_{348}$ are each independently hydrogen or $C_{1-6}$ alkyl), or —$Y_{71}$-tetrazol-5-yl (wherein $Y_{71}$ is a bond, vinylene, methyleneoxymethylene, methylene (each optionally substituted by $C_{1-6}$ alkyl, one or two benzyl groups, thienylmethyl, furylmethyl) or a group of formula —$C(O)NHCHR_{349}$—, (wherein $R_{349}$ is hydrogen, $C_{1-6}$ alkyl, phenyl, benzyl, thienylmethyl, or furylmethyl));

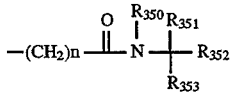

(xxxi)

wherein $R_{350}$ and $R_{351}$ are each independently hydrogen or $C_{1-6}$ alkyl; $R_{352}$ is hydrogen, $C_{1-8}$ alkyl, or a group of formula thienyl—$Y_{80}$—, furyl—$_{80}$—, pyrazolyl—$Y_{80}$—, imidazolyl—$Y_{80}$—, thiazolyl—$Y_{80}$—, pyridyl—$Y_{80}$—, tetrazolyl—$Y_{80}$—, pyrrolyl—$Y_{80}$—, triazolyl—$Y_{80}$—, oxazolyl—$Y_{80}$—, isoxazolyl—$Y_{80}$— or phenyl—$Y_{80}$— (wherein $Y_{80}$ is a bond or $C_{1-6}$ alkylene) with each aryl or heteroaryl group optionally substituted by $C_{1-6}$ alkyl, $C_{1-6}$ alkoxy, $C_{1-4}$ perfluoroalkyl, $C_{1-6}$ alkylthio, $C_{1-6}$ alkylsulphonyl, $C_{1-4}$ perfluoroalkylsulphonyl, halo, hydroxy, nitro or a group of formula —$NR_{354}R_{355}$, —$CO_2R_{354}$, —$SO_2NHR_{354}$, —$SO_3H$, —$CONR_{354}R_{355}$, —$NR_{354}CHO$, —$NR_{354}COR_{356}$, or —$NR_{354}COC_{1-6}$ alkyl (wherein $R_{354}$ and $R_{355}$ are each independently hydrogen or $C_{1-4}$ alkyl and $R_{356}$ is $C_{1-4}$ perfluoroalkyl); $R_{353}$ is a group of formula —$CO_2R_{358}$, —$CONR_{358}R_{357}$, or tetrazol-5-yl (wherein $R_{357}$ and $R_{358}$ are each hydrogen or $C_{1-6}$ alkyl); and n is 0 or an integer from 1 to 5;

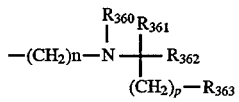

(xxxii)

wherein $R_{360}$ is hydrogen, $C_{1-6}$ alkyl, $C_{3-6}$ alkenyl, $C_{1-5}$ alkylcarbonyl, or a group of formula —$(CH_2)_{0-3}$ phenyl; $R_{361}$ is hydrogen, $C_{1-6}$ alkyl, $C_{3-6}$ alkenyl, or —$(CH_2)_{0-3}$ phenyl; $R_{362}$ is a group of formula —CO$_2$R$_{364}$, —CONR$_{364}$R$_{365}$, (wherein R$_{364}$ and R$_{365}$ are each independently hydrogen or C$_{1-6}$ alkyl) or tetrazol-5-yl;

n and p are each independently 0 or an integer from 1 to 4; and

R$_{363}$ is phenyl, naphthyl, thienyl, furyl, pyridyl, pyrimidyl, imidazolyl, thiazolyl, triazolyl, tetrazolyl, pyrazolyl, pyrrolyl, oxazolyl, or isoxazolyl, with each aryl or heteroaryl group optionally substituted by C$_{1-6}$ alkyl, C$_{1-6}$ alkoxy, halo, fluoro, hydroxy, nitro, C$_{1-4}$ perfluoroalkyl, C$_{1-6}$ alkylsulphonyl, C$_{1-4}$ perfluoroalkylsulphonyl, C$_{1-6}$ alkylthio, or a group of formula —NR$_{366}$R$_{367}$, —CO$_2$R$_{366}$, —CONR$_{366}$R$_{367}$, —SO$_3$H, —SO$_2$NHR$_{366}$, —NR$_{366}$CHO; —NR$_{366}$CO (C$_{1-4}$ perfluoroalkyl or —NRCOC$_{1-6}$ alkyl (wherein R$_{366}$ and R$_{367}$ are each independently hydrogen or C$_{1-6}$ alkyl);

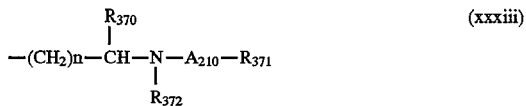
(xxxiii)

wherein R$_{370}$ is a group of formula —CO$_2$R$_{373}$, CONR$_{373}$R$_{374}$, or tetrazol-5-yl; A$_{210}$ is a bond or a carbonyl group; R$_{371}$ is hydrogen, C$_{1-8}$ alkyl, C$_{3-6}$ cycloalkyl, phenyl, phenyl C$_{1-4}$ alkylene or biphenyl or biphenyl C$_{1-3}$ alkylene wherein each phenyl group is optionally substituted by to three substituents selected from C$_{1-6}$ alkyl, nitro, halo, fluoro, hydroxy, C$_{1-6}$ alkyl, or a group of formula —NR$_{375}$R$_{376}$, —CO$_2$R$_{376}$, or —CONR$_{375}$R$_{376}$ (wherein R$_{375}$ and R$_{376}$ are each independently hydrogen or C$_{1-4}$ alkyl); R$_{372}$ is hydrogen or C$_{1-6}$ alkyl ; R$_{373}$ and R$_{374}$ are independently hydrogen, C$_{1-4}$ alkyl, or a group of the formula —(CH$_2$)$_{0-4}$ phenyl; and n is 0 or an integer from 1 to 4.

In preferred compounds of formula V, B$_{60}$ is 1,4-phenylene, optionally substituted as in the definition above.

Preferred compounds of formula V are represented by formula VI:

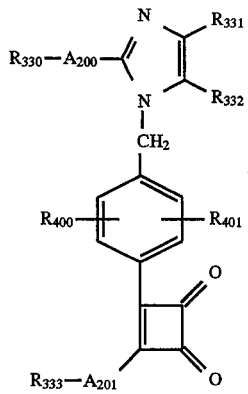
VI wherein R$_{330}$, A$_{200}$, R$_{331}$, R$_{332}$, A$_{201}$ and R$_{333}$ are each as defined above, and R$_{400}$ and R$_{401}$ are each independently hydrogen, halo, fluoro, C$_{1-4}$ alkyl, nitro, hydroxy, C$_{1-4}$ alkoxy, C$_{1-4}$ alkylsulphonyl, C$_{1-3}$ perfluoroalkyl, nitrilo or a group of formula —SO$_2$NHR$_{402}$, —NHSO$_2$R$_{402}$ or —CONR$_{402}$R$_{403}$ (wherein R$_{402}$ and R$_{403}$ are each hydrogen or C$_{1-4}$ alkyl); and the other substituents are each as defined above.

Where not otherwise indicated, the terms "alkyl", "alkenyl", and "alkynyl" as used above denote straight or branched radicals having from 1 to 10 carbon atoms, preferably 1 to 6 carbon atoms and more preferably from 1 to 4 carbon atoms.

Where not otherwise indicated, the term "aryl" as used above denotes phenyl or naphthyl, optionally substituted with halo, fluoro, C$_{1-4}$ alkyl, C$_{1-4}$ alkoxy, nitro, trifluoromethyl, C$_{1-4}$ alkylthio, hydroxy, amino, di(C$_{1-4}$ alkyl)amino, carboxy or carboxy esterified with C$_{1-4}$ alkyl.

Where not otherwise indicated, the term "heteroaryl" as used above denotes a five or six membered aromatic ring containing up to 3 of oxygen, nitrogen and/or sulphur and optionally substituted by hydroxy, sulphydryl, C$_{1-4}$ alkyl, C$_{1-4}$ alkoxy, trifluoromethyl, halo, fluoro, nitro, carboxy, carboxy esterified with C$_{1-4}$ alkyl, amino, C$_{1-4}$alkylamino or di(C$_{1-4}$ alkyl)amino.

It will be understood that a group containing a chain of 3 or more carbon atoms may be straight or branched, for example, propyl includes n-propyl and isopropyl and butyl includes n-butyl, sec-butyl, isobutyl and tert-butyl. The term "halo" as used herein signifies bromo, chloro or iodo.

Specific compounds of the present invention are:

3-[4'-(2-ethyl-5,7-dimethyl-3H-imidazo[4,5-b]pyrid-3-ylmethyl)biphenyl-2-yl]-4-isopropoxycyclobut-3 -ene-1,2-dione;

3-[4'-(2-ethyl-5,7-dimethyl-3H-imidazo[4,5-b]pyrid-3-ylmethyl)biphenyl-2-yl]-4-hydroxycyclobut-3-ene-1,2-dione;

3-amino-4-[4'-(2-ethyl-5,7-dimethyl -3H-imidazo[4,5-b] pyrid-3 -ylmethyl)biphenyl-2-yl]cyclobut-3-ene-1,2-dione;

3-[4'-(5,7-dimethyl-2-propyl-3H-imidazo[4,5-b]pyrid-3-ylmethyl)biphenyl-2 -3,1]-4-isopropoxycyclobut-3-ene-1,2-dione;

3-[4'-(5,7-dimethyl-2-propyl-3H-imidazo[4,5-b]pyrid-3-ylmethyl)biphenyl-2-yl]-4-hydroxycyclobut-3-ene-1,2-dione;

2-ethyl-3-[2'-(2-isopropoxy-3,4-dioxocyclobut-1-en-1-yl) biphenyl-4-ylmethyl]-5,7, N,N-tetramethyl-3H-imidazo [4,5-b]pyridine-6-sulphonamide;

2-ethyl-3-[2'-(2-hydroxy-3,4-dioxocyclobut-1-en-1-yl) biphenyl-4-ylmethyl]-5,7, N,N-tetramethyl-3H-imidazo-[4,5-b]pyridine-6-sulphonamide;

3-[4'-(6-chloro-2-ethyl-5,7-dimethyl-3H-imidazo[4,5-b]-pyrid-3-ylmethyl)biphenyl-2-yl]-4-hydroxycyclobut-3-ene-1,2-dione;

2-[4'-(2 -ethyl-5,7-dimethyl-3H-imidazo[4,5-b]pyrid3-ylmethyl)biphenyl-2-yl]-3,4-dioxocyclobut-1-en-1 -yloxymethyl pivalate;

4-ethyl-1-[2'-(3,4-dioxo-2-isopropoxycyclobut-1-en-1-yl) biphenyl-4-ylmethyl]-2-propyl-1H-imidazole-5-carboxaldehyde;

4-ethyl-1-[2'-(2-hydroxy-3,4-dioxocyclobut-1-en-1-yl) biphenyl-4-ylmethyl]-2-propyl-1H-imidazole-5-carboxaldehyde;

3-dimethylamino-4-[4'-(2-ethyl-5,7-dimethyl-3H-imidazo [4,5-b]pyrid-3-ylmethyl)biphenyl-2-yl]cyclobut-3-ene-1, 2-dione;

1-[2-[4'-(2-ethyl-5,7-dimethyl-3H-imidazo[4,5-b]pyrid3-ylmethyl)biphenyl-2-yl]-3,4-dioxocyclobut-1-en-1-yloxy]ethyl pivalate;

ethyl 4-[N-butyl-N-[2'-(2-isopropoxy-3,4-dioxocyclobut-1-en-1-yl)biphenyl-4-ylmethyl]amino]pyrimidine-5-carboxylate;

ethyl 4-[N-butyl-N-[2'-(2-hydroxy-3,4-dioxocyclobut-1-en-1-yl)biphenyl-4-ylmethylamino]pyrimidine-5-carboxylate;

4-[N-butyl-N-[2'-(2-hydroxy-3,4-dioxocyclobut-1-en-1-yl)-biphenyl-4-ylmethylamino]pyrimidine-5-carboxylic acid;

3-[4'-(2-butyl-5-oxo-2-imidazoline-4-spirocyclopent-1-ylmethyl)biphenyl-2-yl]-4-isopropoxycyclobut-3-ene-1, 2-dione;

3-[4'-(2-butyl-5-oxo-2-imidazoline-4-spirocyclopent-1-ylmethyl)biphenyl-2-yl]-4-hydroxycyclobut-3-ene-1,2-dione;

2-butyl-4-chloro-1-[2'-(2-isopropoxy-3,4-dioxocyclobut-1-en-1-yl)biphenyl-4-ylmethyl)]-1H-imidazole-5-carboxaldehyde;

2-butyl-4-chloro-1-[2'-(2-hydroxy-3,4-dioxocyclobut-1-en-1-yl)biphenyl-4-ylmethyl]-1H-imidazole-5-carboxaldehyde;

3-[4'-(2-butyl-4-chloro-5-hydroxymethyl-1H-imidazol-1-ylmethyl)biphenyl-2-yl]-4-isopropoxycyclobut-3-ene-1,2-dione;

methyl 2-butyl-4-chloro-1-[2'-(2-isopropoxy-3,4-dioxocyclobut-1-en-1-yl)biphenyl-4-ylmethyl]-1H-imidazole-5-carboxylate;

methyl2-butyl-4-chloro-1-[2'-(2-hydroxy-3,4-dioxocyclobut-1-en-1-yl)biphenyl-4-ylmethyl)-1H-imidazole-5-carboxylate;

2-butyl-4-chloro-1-[2'-(2-hydroxy-3,4-dioxocyclobut-1-en-1-yl)biphenyl-4-ylmethyl]-1H-imidazole-5 -carboxylic acid; and (E)-2-benzyl-3-[2-butyl-4-chloro-1-[4(2-hydroxy-3,4-dioxocyclobut-1-en-1-ylbenzyl]-1H-imidazol-5-yl] propenoic acid;

and, where appropriate, pharmaceutically acceptable salts and/or solvates thereof, such as alkali metal salts, preferably sodium salts, and hydrochlorides.

The present invention also provides compounds of formula I to Vi wherein $A_{51}$, $A_{190}$ and $A_{201}$ are each oxygen modified in that $R_{50}$, $R_{310}$ and $R_{333}$ are each a group capable of being hydrolysed in vivo to leave compounds of formula I to VI wherein $R_{50}$, $R_{310}$ and $R_{333}$ are hydrogen, such groups including groups of formula xxxv

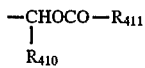
(xxxv)

wherein $R_{410}$ is hydrogen or $C_{1-4}$ alkyl and $R_{411}$ $C_{1-4}$ alkyl or $C_{3-6}$cycloalkyl; those of formula xxxvi

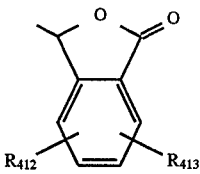
(xxxvi)

wherein $R_{412}$ and $R_{413}$ are each independently hydrogen or $C_{1-4}$ alkyl; and those of formula xxxvii

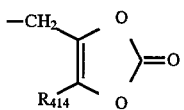
(xxxvii)

wherein $R_{414}$ is hydrogen or $C_{1-4}$ alkyl.

Compounds bearing such groups are commonly described as 'pro-drugs'. It will be appreciated by a person skilled in the art that a wide variety of other groups which are removable in vivo may be used in such 'pro-drugs'. Examples of such groups and methods for their addition can be found in an article by H. Bundgaard, (Drugs of the Future (1991), 16, 443) and in the books "Design of Prodrugs" (Editor H Bundgaard, 1985 Elsevier Science Publishers BV, Biomedical Division) and "Pro-drugs as Novel Drug Delivery Systems" (Editors T. Higuchi and V. Stella, 1975, ACS Symposium Series 14, American Chemical Society, Washington, D.C.). Unless otherwise stated, all references below to 'compounds of formula I to VI' include, where appropriate, such 'pro-drugs' of compounds of formula I to VI.

Compounds of formula I to VI may form salts with acids or bases. Reference hereinafter to compounds of formula I to VI includes all such salts of compounds of formula I to VI which are pharmaceutically acceptable. Particularly suitable salts of compounds of formula I to VI include, for example, alkali metal salts (such as sodium and potassium salts), alkaline earth metal salts (such as magnesium and calcium salts), aluminum and ammonium salts, salts with suitable organic bases such as alkylamines, N-methyl-D-glucamine and salts with amino acids such as arginine and lysine. Also suitable are salts with inorganic acids, for example hydrochlorides, hydrobromides, sulphates and phosphates, and salts with organic acids, for example maleates and fumarates.

It will be appreciated by those skilled in the art that certain compounds of formula I to VI or their salts contain one or more chiral centres. When a compound of formula I to VI contains a single chiral centre it may exist in two enantiomeric forms which may be obtained separately by methods known to those skilled in the art. Such methods typically include resolution via formation of diastereoisomeric salts or complexes which may be separated, for example, by crystallisation; formation of diastereoisomeric derivatives which may be separated, for example, by crystallization, gas-liquid or liquid chromatography; selective derivatisation of one enantiomer by reaction with an enantiomer-specific reagent, for example enzymatic oxidation or reduction; or gas-liquid or liquid chromatography in a chiral environment, for example on a chiral support or in the presence of a chiral solvent. Alternatively, specific enantiomers may be synthesised by asymmetric synthesis using optically active reagents, substrates, catalysts or solvents, or converting one enantiomer into the other by asymmetric transformation. The present invention includes each enantiomer of compounds of formula I to VI and mixtures thereof. When a compound of formula I to VI contains more than one chiral centre it may exist in diastereoisomeric forms. The diastereoisomers may be separated by methods known to those skilled in the art, for example chromatography or crystallisation. The present invention includes each diastereoisomer of compounds of formula I to VI and mixtures thereof. It will be appreciated that where the active moiety is transformed by the separation procedures described above, a further step is required to convert the product to the active moiety.

Certain compounds of formula I to VI or their salts may exist in more than one crystal form and the present invention includes each crystal form and mixtures thereof.

Certain compounds of formula I to VI may exist in zwitterionic form and the present invention includes each zwitterionic form and mixtures thereof.

Certain compounds of formula I to Vl or their salts may also exist in the form of solvates, for example hydrates, and the present invention includes each solvate and mixtures thereof.

The present invention also provides pharmaceutical compositions which comprise a compound of formula I to VI or salts thereof together with a pharmaceutically acceptable diluent or carrier. Specific compounds which may be incorporated into the compositions of this invention are the novel compounds disclosed above.

As used hereinafter, the term "active compound" denotes a compound of formula I to VI, preferably formula II. In therapeutic use the active compound may be administered orally, rectally parenterally or topically, preferably orally Thus the therapeutic compositions of the present invention may take the form of any of the known pharmaceutical compositions for oral, rectal, parenteral or topical administration. The compositions may be formulated in a manner known to those skilled in the art so as to give a controlled release of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art.

Tablets may be prepared by mixing the active compound with an inert diluent, such as lactose or calcium phosphate, in the presence of disintegrating agents, for example maize starch, and lubricating agents, for example magnesium stearate, and tableting the mixture by known methods. Such tablets may if desired be provided with enteric coatings by known methods, for example by the use of cellulose acetate phthalate. Similarly capsules, for example hard or soft gelatin capsules containing the active compound with or without added excipients, may be prepared by conventional means and, if desired, provided with enteric coatings in a known manner. Enteric coated compositions of the invention may be advantageous, depending on she nature of the active compound. The tablets and capsules may conveniently each contain 1–500 mg of the active compound. Other compositions for oral administration include, for example, aqueous suspensions containing the compound of formula I to VI in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the compound of formula I to VI transdermally. Alternatively the active compound may be dispersed in a cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example a β-adrenoceptor antagonist such as atenolol, propranolol, oxprenolol, nadolol or timolol, and/or a diuretic such as bendrofluazide, ethacrynic acid or frusemide, and/or an angiotensin converting enzyme inhibitor such as captopril or enalapril, and/or vasodilators such as hydralazine hydrochloride, flosequinan, sodium ninroprusside, glyceryl trinitrate or molsidomine, and/or potassium channel activators such as lemakalim or pinacidil, and/or an α-adrenoceptor antagonist such as prazosin or labetalol, and/or other hypotensives such as clonidine, diazoxide, α-methyldopa or ketanserin, and/or positive inotropes such as milrinone, digitalis or dobutamine, and/or PDE inhibitors such as zaprinast, and/or specific bradycardic agents such as alinidine or falipamil, an endothelin antagonist and/or an endothelin converting enzyme inhibitor, and/or a renin inhibitor, and/or a thrombolytic agent such as streptokinase.

The therapeutic activity of compounds of formula I to VI has been demonstrated by means of tests on standard laboratory animals. Such tests include, for example, the oral administration of the compounds to a strain of spontaneously hypertensive rat. Thus, compounds of formula I to VI are useful for reducing blood pressure in hypertensive mammals. Whilst the precise amount of active compound administered will depend on a number of factors, for example the age of the patient, the severity of the condition and the past medical history and always lies within the sound discretion of the administering physician, a suitable dose for enteral administration to mammals, including humans, is generally within the range 0.01–25 mg/kg/day, more usually 0.2–10 mg/kg/day given in single or divided doses. For parenteral administration, a suitable dose is generally within the range 0.001–2.5 mg/kg/day, more usually 0.005–1 mg/kg/day given in single or divided doses or by continuous infusion. Oral administration is preferred.

Compounds of formula I to VI and salts thereof are angiotensin II antagonists and therefore are useful in the treatment of hypertension in mammals, including humans. Compounds of formula I to VI are also indicated as suitable for use in the treatment of acute and chronic congestive heart failure, glaucoma, primary and secondary hyperaldosteronism, primary and secondary pulmonary hypertension cor pulmonale, renal failure, renal vascular hypertension, angina, migraine, left ventricular dysfunction, peripheral vascular disease (eg Raynaud's disease), scleroderma, diabetic nephropathy, and prevention of coronary insufficiency after myocardial infarction.

Accordingly, the present invention further provides a method for treatment of the said conditions, the use of any compound of formula I to VI in the treatment of the said conditions and the use of any compound of formula I to VI in the manufacture of a medicament for the treatment of the said conditions.

Processes for the preparation of compounds of formula I will now be described. These processes form a further aspect of the present invention.

Compounds of formula I wherein $R_{50}$ is $C_{1-4}$ alkyl, $A_{51}$ is oxygen and r is 1 may be prepared by reacting a compound of formula X

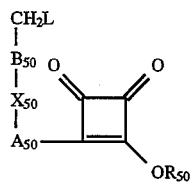

wherein L is a leaving group such as halo (e.g. bromo); and $R_{50}$ is $C_{1-4}$ alkyl; with a corresponding compound of formula Het-H, wherein Het is as defined in the lists of structural formulae above; in a solvent inert to the conditions of the reaction; preferably in the presence of a base.

Compounds of formula Het-H may be prepared by methods described in the corresponding patent publications identified above. In particular, compounds of formula Het-H wherein Het is a group of formula xxv, xxvii and xxviii may be prepared as described in EP-A-0400974 (Merck), WO-A-9114679 (Sanofi) and EP-A-0475206 (Abbott) respectively.

Compounds of formula Het-H wherein Het is a group of formula xxvi, may be prepared by methods described in Schunack [Arch. Pharmaz. (1974) Vol. 307, p46] (for compounds wherein $R_8$ is hydrogen), EP-A-0253310 (for compounds wherein $R_8$ is chloro or trifluoromethyl), EP-A-0324337 (for compounds wherein $R_8$ is pentafluoroethyl), WO-A-9200977 (for compounds wherein $R_8$ is $C_{1-4}$ alkyl) and EP-A-0465368 (for compounds wherein $R_8$ is $C_{1-4}$ alkylsulphinyl, $C_{1-4}$ alkylsulphonyl, $C_{1-4}$ alkylthio, arylsulphinyl, arylsulphonyl, arylthio, arylmethylsulphinyl, arylmethylsulphonyl or arylmethylthio [wherein "aryl" denotes phenyl optionally substituted by $C_{1-4}$ alkyl, $C_{1-4}$ alkoxy or fluoro, chloro or bromo]).

Compounds of formula X wherein L is halo, for example chloro or bromo, may be prepared by reaction of a compound of formula XI

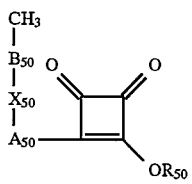
XI with a chlorinating agent, for example benzyltriethylammonium tetrachloroiodate, or a brominating agent, for example N-bromosuccinimide; in a solvent inert to the conditions of the reaction.

Compounds of formula XI wherein $X_{50}$ is a bond such that $A_{50}$ and $B_{50}$ are directly bonded via a carbon-carbon bond (i.e. when $A_{50}$ is a group of formula ii, iii, iv or v above and $B_{50}$ is a group of formula xv, xix, xx, xxi or xxii) may be prepared by reacting a compound of formula XII

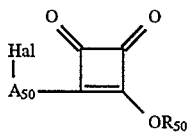
XII wherein Hal is halo, suitably bromo or iodo; with a compound of formula XIII

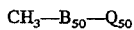
CH₃—B₅₀—Q₅₀    XIII wherein $B_{50}$ is a group of formula xv, xix, xx, xxi or xxii above; and $Q_{50}$ represents a group known for the coupling of aromatic species such as a boronic acid group of formula —B(OH)₂ or a boronic acid derivative of formula —B(OAlk)₂ (wherein Alk represents a $C_{1-4}$ alkyl group) or a trialkyl stannyl group of formula —Sn(Alk)₃ (wherein Alk represents a $C_{1-4}$ alkyl group); in a solvent inert to the conditions of the reaction; preferably by reaction in the presence of a base, such as sodium carbonate; suitably in the presence of a metal catalyst, such as a palladium(0) or nickel(0) catalyst, or by reacting in the same way compounds of formula XII and XIII modified in that substituents $Q_{50}$ and Hal therein are interchanged.

Compounds of formula XIII wherein $B_{50}$ is a group of formula xv, xix, xx, xxi or xxii above are either known from the patent publications identified by the letters (m) and (q) to (t) above or are readily derivable from compounds described therein by methods well-known in the art (for example by a boronation reaction in which a compound of formula XIII modified in that $Q_{50}$ is lithium or a group of formula MgHal (wherein Hal is halo) is reacted with a trialkyl borate (such as triisopropyl borate at from −100° C. to 0° C.) in a solvent (such as tetrahydrofuran) inert to the conditions of the reaction. Hydrolysis in the presence of an acid such as hydrochloric acid may if desired be carried out to produce a substituent of formula —B(OH)₂ on the compound of formula XIII).

Compounds of formula XII may be prepared by reacting a compound of formula XIV

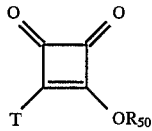
XIV wherein T is a trialkylstannyl group of formula —Sn(Alk)₃ wherein Alk represents a $C_{1-4}$ alkyl group (suitably a butyl group); with a compound of formula XV

Hal—A₅₀—I    XV wherein Hal is bromo or iodo, suitably bromo; in a solvent inert to the conditions of the reaction, suitably in the presence of a metal catalyst, such as a palladium(0) or nickel(0) catalyst.

Compounds of formula XIV may be prepared as described by Liebeskind and Fengl in Journal of Organic Chemistry (1990) Vol. 55 pp 5359/5364.

Compounds of formula XV are either known from the patent publications identified by the letters (b) to (e) above, or are readily preparable from compounds described therein, for example by appropriate use of halogenation reactions as described above.

Compounds of formula XI may also be prepared by reacting a compound of formula XVI

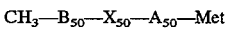
CH₃—B₅₀—X₅₀—A₅₀—Met    XVI wherein Met is lithium or a group of formula MgX wherein X is chloro, bromo or iodo; with a compound of formula XVII

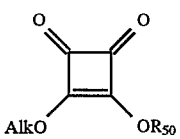
XVII wherein Alk is $C_{1-4}$ alkyl; followed by treatment with an acylating agent, for example, with trifluoroacetic anhydride; in a solvent inert to the conditions of the reaction.

Compounds of formula XVII are available commercially from Aldrich Chemical Co. (UK).

Compounds of formula XVI may be prepared by reacting a compound of formula XVIII

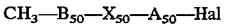
CH₃—B₅₀—X₅₀—A₅₀—Hal    XVIII wherein Hal is halo, preferably bromo; with a $C_{1-4}$ alkyl lithium compound or magnesium metal; in a solvent inert to the conditions of the reaction.

Compounds of formula XVII I wherein $X_{50}$ is a bond such that $A_{50}$ and $B_{50}$ are bonded via a carbon-carbon bond (i.e. when $A_{50}$ is a group of formula ii, iii, iv or v above and $B_{50}$ is a group of formula xv, xix, xx, xxi or xxii) may be prepared by reacting a compound of formula XIII above with a compound of formula XIX

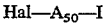
Hal—A₅₀—I    XIX wherein Hal is halo or iodo and $A_{50}$ is a group of formula ii, iii, iv or v above; in a solvent inert to the conditions of the reaction; preferably by reaction in the presence of a base such as sodium carbonate; suitably in the presence of a metal catalyst, such as a palladium(0) or nickel(0) catalyst; or by reacting in the same way compounds of formula XIII and XIX modified in that the substituents $Q_{50}$ and Hal therein are interchanged.

Compounds of formula XVIII wherein $X_{50}$ is a bond such that $A_{50}$ and $B_{50}$ are bonded via a carbon-carbon bond (i.e. when $A_{50}$ is a group of formula ii, iii, iv or v above and $B_{50}$ is a group of formula xv, xix, xx, xxi or xxii) may also be prepared by reacting a compound of formula XIII in which $Q_{50}$ is a group of formula —MgHal (wherein Hal is bromo or chloro) with a compound of formula XX

  XX wherein $A_{50}$ is a group of formula ii, iii, iv or v above and each Hal is independently chloro, bromo or iodo; in a solvent inert to the conditions of the reaction; preferably by reaction in the presence of a base, such as sodium carbonate; suitably in the presence of a metal catalyst, such as a palladium(0) or nickel(0) catalyst, or by reacting in the same way compounds of formula XIII and XX modified in that the substituents $Q_{50}$ and Hal therein are interchanged.

Compounds of formula XIX and XX are either known from the patent publications identified by the letters (b) to (e) above, or are readily preparable from compounds described therein.

Compounds of formula I wherein $A_{51}$ is oxygen, r is 1 and $R_{50}$ is $C_{1-4}$ alkyl may also be prepared by reacting a compound of formula XXI

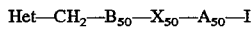  XXI with a compound of formula XIV above; in a solvent inert to the conditions of the reaction; suitably in the presence of a metal catalyst; for example a palladium (0) or nickel(0) catalyst.

Compounds of formula XXI may be prepared by reacting a compound of formula XXII

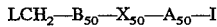  XXII wherein L is a leaving group, suitably halo, (e.g. bromo or chloro) with a compound of the formula Het-H as described above; in a solvent inert to the conditions of the reaction; preferably in the presence of a base.

Compounds of formula XXI may also be prepared by reacting a compound of formula XXII (or a corresponding compound wherein L is amino) with a precursor of the corresponding group of formula Het, and then generating the Het moiety in situ. Suitable methods are described in the patent publications identified above.

Compounds of formula XXII wherein L is bromo or chloro may be prepared by reacting a compound of formula XXIII

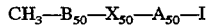  XXIII with a chlorinating agent, for example benzyltriethylammonium tetrachloroiodate, or a brominating agent, for example N-bromosuccinimide; in a solvent inert to the conditions of the reaction.

Compounds of formula XXIII above wherein X is a bond such that $A_{50}$ and $B_{50}$ are bonded via a carbon-carbon bond (i.e. when $A_{50}$ is a group of formula ii, iii, iv or v above and $B_{50}$ is a group of formula xv, xix, xx, xxi or xxii) may be prepared by reacting a compound of formula XIII -above with a compound of formula XIX above; in a solvent inert to the conditions of the reaction; preferably by reaction in the presence of a base such as sodium carbonate; suitably in the presence of a metal catalyst, such as a palladium(0) or nickel(0) catalyst, or by reacting in the same way compounds of formula XIII and XIX modified in that the substituents $Q_{50}$ and Hal therein are interchanged.

It will be appreciated that where a compound of formula Het-H or a group of formula Het contains a reactive substituent, such as carboxy, it may be necessary to protect this substituent (for example by esterification in the case of carboxy) before some of the reactions described above are carried out. After such reaction, the substituent may be deprotected (for example by acid or alkaline hydrolysis) to provide the free substituent as required.

Compounds of formula I wherein $A_{50}$ is a group of formula vii above, $R_{50}$ is $C_{1-4}$ alkyl, $X_{50}$ is a bond, r is 1 and $A_{51}$ is oxygen may be prepared by reaction of a compound of formula XL

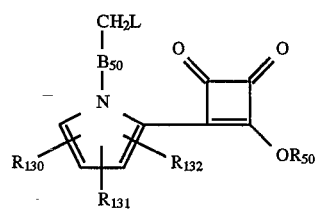  XL wherein L is a leaving group such as halo, (e.g. bromo); and $R_{50}$ is $C_{1-4}$ alkyl; with a corresponding compound of formula Het-H, wherein Het is as defined in the lists of structural formulae above; in a solvent (such as dimethylformamide) inert to the conditions of the reaction; preferably in the presence of a base, such as sodium hydride.

Compounds of formula XL wherein $R_{50}$ is $C_{1-4}$ alkyl and L is halo, for example chloro or bromo, may be prepared by reaction of a compound of formula XLI

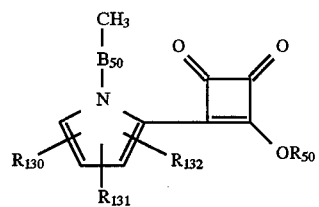  XLI with a chlorinating agent, for example benzyltriethylammonium tetrachloroiodate, or a brominating agent, for example N-bromosuccinimide; in a solvent inert to the conditions of the reaction.

Compounds of formula XLI may be prepared by reacting a compound of formula XLII

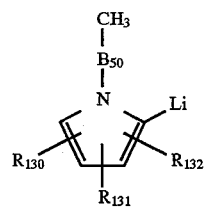  XLII with a compound of formula XVII above followed by an acylating agent, for example trifluoroacetic anhydride; in a solvent inert to the conditions of the reaction.

Compounds of formula XLII may be prepared by reacting a compound of formula XLIII

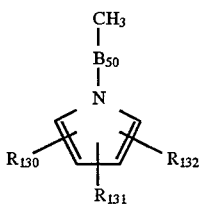

XLIII with a $C_{1-4}$ alkyllithium reagent, (such as butyllithium); in a solvent inert to the conditions of the reaction.

Compounds of formula XLIII are known from WO-A-9215577 (Searle).

Compounds of formula I wherein $X_{50}$ is not a bond but is a spacer group as defined above may be prepared by reactions as above, modified by use of appropriate alternative aromatic or aliphatic coupling reactions as identified in FR-A-2669928 (Labs UPSA), EP-A-0323841 (Du Pont), EP-A-0475206 (Abbott), EP-A-0449699 (Labs UPSA), U.S. Pat. No. 5091390 (Du Pont), US-A-4880804 Du Pont) and U.S. Pat. No. 5043349 (Du Pont) and the references therein.

Compounds of formula V wherein $A_{201}$ is oxygen and $R_{333}$ is $C_{1-4}$ alkyl may be prepared by reacting a compound of formula L

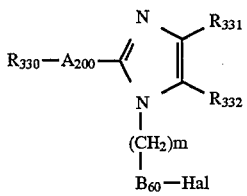

L with a compound of formula XIV above (wherein $R_{50}$ is $R_{333}$); in a solvent inert to the conditions of the reaction; suitably in the presence of a metal catalyst such as a palladium(0) or nickel 0) catalyst.

Compounds of formula L wherein $R_{332}$ is a group of formula xxx may be prepared by dehydrating a compound of formula LI

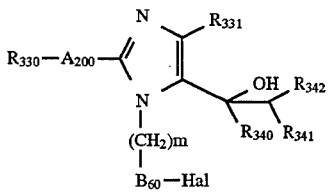

LI for example by reaction with an acylating agent such as acetic anhydride, followed by a base, such as diazobicyclo [5.4.0]undec-7-ene; in a solvent inert to the conditions of the reaction.

Compounds of formula LI may be prepared by reacting a compound of formula LII

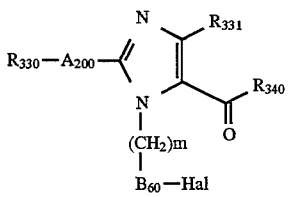

LII with a compound of formula $R_{341}CH_2R_{342}$; in a solvent inert to the conditions of the reaction; in the presence of a base, such as lithium diisopropylamide. Compounds of formula $R_{341}CH_2R_{342}$ are well-known in the art (e.g. from EP-A-0425211; Smithkline Beecham).

Compounds of formula LII may be prepared by reacting a compound of formula LIII

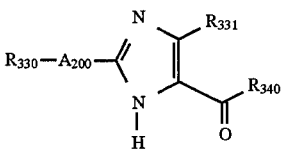

LIII with a compound of formula LIV

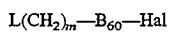

LIV wherein Hal is bromo or iodo and L is a leaving group such as bromo or chloro; in a solvent inert to the conditions of the reaction; suitably in the presence of a base, such as potassium carbonate. This reaction may give rise to a mixture of isomeric products which may be separated by conventional means, for example by flash column chromatography.

Compounds of formula LIII are known from EP-A-0425211 (Smithkline Beecham) or are readily derivable from compounds described therein by methods well-known in the art.

Compounds of formula LIV are well-known in the art.

Compounds of formula L wherein $R_{332}$ is a group of formula xxxi may be prepared by reacting a compound of formula LV

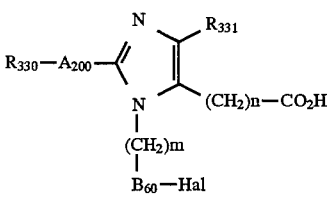

LV wherein Hal is bromo or iodo with a compound of formula LVI

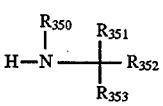

LVI in a solvent inert to the conditions of the reaction; suitably in the presence of a catalyst, such as N-hydroxysuccinimide.

Compounds of formula LV may be prepared as described in EP-A-0437103 (Smithkline Beecham).

Compounds of formula LVI may be prepared as described in EP-A-0437103 (Smithkline Beecham).

Compounds of formula L wherein $R_{332}$ is a group of formula xxxii may be prepared by reacting a compound of formula LVII

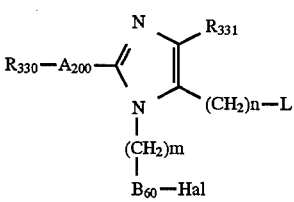

LVII wherein Hal is bromo or chloro and L is a leaving group such as chloro; with a compound of formula LVIII

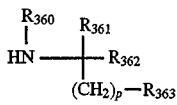
LVIII in a solvent (such as dimethylformamide) inert to the conditions of the reaction; suitably in the presence of a base, such as triethylamine.

Compounds of formula LVIII may be prepared as described in EP-A-0427463 (Smithkline Beecham).

Compounds of formula LVII wherein n is greater than 1, are known from U.S. Pat. No. 4340598 (Takeda) or are readily derivable from compounds described therein by methods well-known in the art.

Compounds of formula LVII wherein L is halo and n is 1 may be prepared by reacting a compound of formula LIX

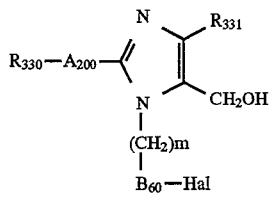
LIX wherein Hal is bromo or chloro; with a halogenating agent, such as thionyl chloride; in a solvent inert to the conditions of the reaction.

Compounds of formula LIX may be prepared by reacting a compound of formula LX

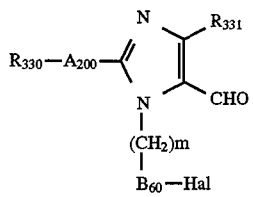
LX with a reducing agent, such as sodium borohydride; in a solvent inert to the conditions of the reaction.

Compounds of formula LX may be prepared as described in EP-A-0427463 (Smithkline Beecham).

Compounds of formula L wherein $R_{332}$ is a group of formula xxxiii wherein $R_{370}$ is carboxyl, $A_{210}$ is carbonyl and $R_{372}$ is $C_{1-6}$ alkyl may be prepared by hydrolysing a compound of formula LXI

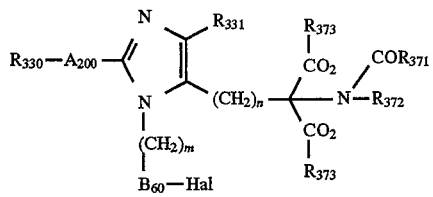
LXI wherein $R_{372}$ is $C_{1-6}$ alkyl and $R_{373}$ is as defined above but is not hydrogen; for example with a base, such as aqueous sodium carbonate solution; in a solvent inert to the conditions of the reaction.

Compounds of formula LXI wherein $R_{372}$ is $C_{1-6}$ alkyl may be prepared by reacting a corresponding compound wherein $R_{372}$ is hydrogen, with a base, such as sodium hydride, followed by a $C_{1-6}$ alkyl halide; in a solvent inert to the conditions of reaction.

Compounds of formula LXI wherein $R_{372}$ is hydrogen may be prepared by reacting a compound of formula LVII above wherein L is chloro with a compound of formula LXII

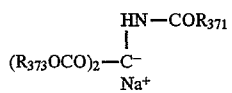
LXII wherein $R_{373}$ is as defined above but is not hydrogen; in a solvent (such as dimethylformamide) inert to the conditions of the reaction.

Compounds of formula LXII may be prepared as described in WO-A-9200068 (Smithkline Beecham).

Compounds of formula L wherein $R_{332}$ is a group of formula xxxiii wherein $R_{370}$ is a group of formula $-CO_2R_{373}$, $A_{210}$ is a bond and $R_{371}$ and $R_{372}$ are both hydrogen may be prepared by hydrolysing a compound of formula LXIII

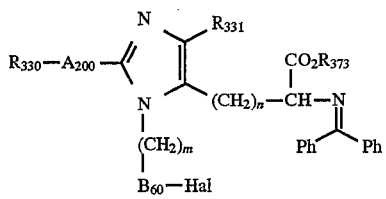
LXIII wherein $R_{373}$ is as defined above but is not hydrogen for example by hydrolysis with dilute aqueous acid, such as hydrochloric acid; in a solvent inert to the conditions of the reaction.

Compounds of formula LXIII may be prepared by reacting a compound of formula LVII wherein L is chloro with a compound of formula LXIV

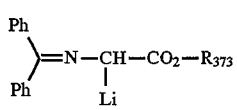
LXIV wherein $R_{373}$ is as defined above except hydrogen; in a solvent (such as tetrahydrofuran) inert to the conditions of the reaction.

Compounds of formula LXIV may be prepared as described in WO-A-9200068 (Smithkline Beecham).

Compounds of formula II, (preferred compounds of the present invention), wherein $R_{310}$ is $C_{1-4}$ alkyl and $A_{190}$ is oxygen may be prepared by reaction of a compound of formula LXX

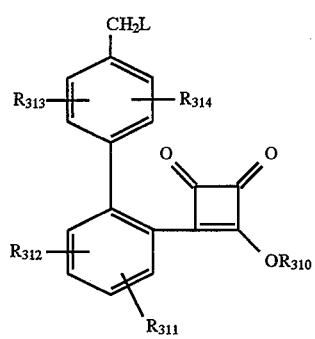
LXX wherein L is a leaving group such as halo and $R_{310}$ is $C_{1-4}$ alkyl; with a corresponding compound of formula Het-H, wherein Het is a group of formula xxxviii

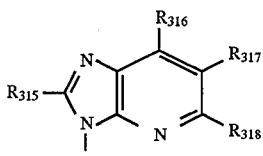

in a solvent inert to the conditions of the reaction; preferably in the presence of a base.

Compounds of formula LXX wherein L is halo, for example chloro or bromo, may be prepared by reaction of a compound of formula LXXI

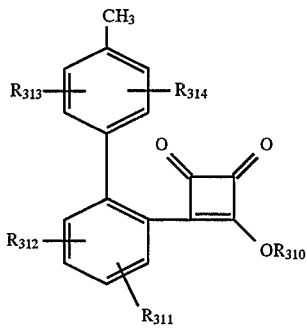

wherein $R_{310}$ is $C_{1-4}$ alkyl; with a halogenating agent such as a chlorinating agent, for example benzyltriethylammonium tetrachloroiodate, or a brominating agent, for example N-bromosuccinimide, in a solvent inert to the conditions of the reaction.

Compounds of formula LXXI may be prepared by reacting a compound of formula LXXII

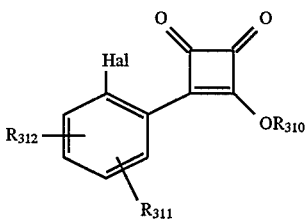

wherein Hal is halo, suitably bromo or iodo and $R_{310}$ is $C_{1-4}$ alkyl; with a compound of formula LXXIII

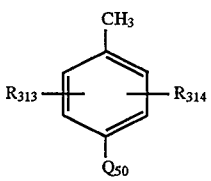

wherein $Q_{50}$ represents a boronic acid group of formula —B(OH)$_2$ or a trialkylstannyl group of formula —Sn(Alk)$_3$ (wherein Alk represents a $C_{1-4}$ alkyl group); in a solvent inert to the conditions of the reaction; preferably by reaction in the presence of a base, such as sodium carbonate; suitably in the presence of a metal catalyst, such as a palladium(0) or nickel(0) catalyst.

Compounds of formula LXXIII are well known in the art.

Compounds of formula LXXII may be prepared by reacting a compound of formula LXXIV

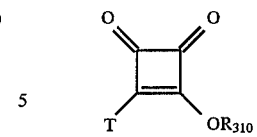

wherein $R_{310}$ is $C_{1-4}$ alkyl and T is a trialkylstannyl group of formula —Sn(Alk)$_3$ wherein Alk represents a $C_{1-4}$ alkyl group, (suitably a butyl group); with a compound of formula LXXV

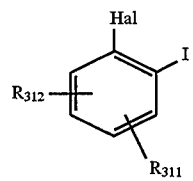

wherein Hal is bromo or iodo, suitably bromo in a solvent inert to the conditions of the reaction, suitably in the presence of a metal catalyst, such as a palladium(0) or nickel(0) catalyst.

Compounds of formula LXXIV may be prepared as described by Liebeskind and Fengl in Journal of Organic Chemistry (1990) Vol.55 pp 5359/5364.

Compounds of formula LXXV are well-known in the art and are available commercially from Lancaster Synthesis Ltd or Aldrich Chemical Co. (UK).

Compounds of formula LXXl may also be prepared by reacting a compound of formula LXXVI

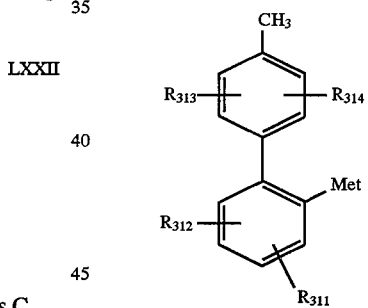

wherein Met is lithium or a group of formula MgX wherein X is chloro, bromo or iodo; with a compound of formula LXXVII

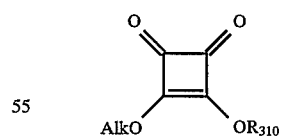

wherein $R_{310}$ is $C_{1-4}$ alkyl and Alk is $C_{1-4}$ alkyl; followed by reaction with an acylating agent, for example, with trifluoroacetic anhydride; in a solvent inert to the conditions of the reaction.

Compounds of formula LXXVII are well-known in the art and are available commercially from Aldrich Chemical Co. (UK).

Compounds of formula LXXVI may be prepared by reacting a compound of formula LXXVIII

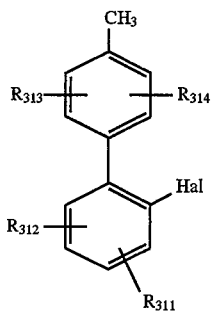

LXXVIII wherein Hal is halo, preferably bromo; with a $C_{1-4}$ alkyl lithium compound or magnesium metal; in a solvent inert to the conditions of the reaction.

Compounds of formula LXXVIII are described in Gomberg and Pernert (J. Am. Chem. Soc. (1926) Vol 48, p1373) and may be obtained as described therein.

They may also be prepared by reacting a compound of formula LXXIII modified in that $Q_{50}$ is a group of formula MgHal (wherein Hal is chloro, bromo or iodo) with 1,2-diiodobenzene, 1,2-bromoiodobenzene, 1,2-dibromobenzene, or 1,2-bromochlorobenzene (substituted with $R_{311\ 1}$ and/or $R_{312}$ groups as appropriate) in a solvent inert to the conditions of the reaction; in the presence of a palladium(0) or nickel(0) catalyst.

Compounds of formula LXXIII modified in that $Q_{50}$ is a group of formula MgHal may be prepared by reacting corresponding compounds wherein $Q_{50}$ is chloro, bromo or iodo with magnesium metal; in a solvent inert to the conditions of the reaction.

Compounds of formula II wherein $A_{190}$ is oxygen and $R_{310}$ is lower alkyl may also be prepared by reacting a compound of formula LXXIX

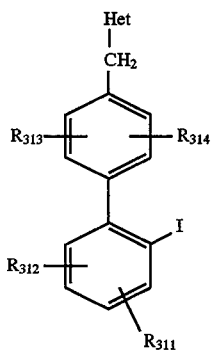

LXXIX wherein Het is a group of formula xxxviii above; with a compound of formula LXXIV above, in a solvent inert to the conditions of the reaction, suitably in the presence of a metal catalyst, for example a palladium(0) or nickel(0) catalyst.

Compounds of formula LXXIX may be prepared by reacting a compound of formula LXXX

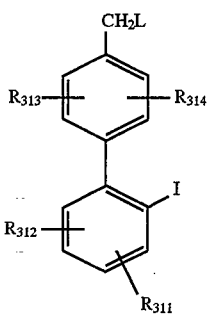

LXXX wherein L is a leaving group, suitably halo, (e.g. bromo or chloro); with a compound of the formula Het-H (wherein Het is a group of formula xxxviii above), in a solvent inert to the conditions of the reaction, preferably in the presence of a base.

Compounds of formula LXXX wherein L is bromo or chloro may be prepared by reacting a compound of formula LXXXI

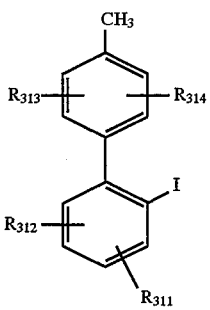

LXXXI with a chlorinating agent, for example benzyltriethylammonium tetrachloroiodate, or a brominating agent, for example, H-bromosuccinimide.

Compounds of formula LXXXI are known from Hammerschmidt and Vogtle (Chem. Bet. (1979) Vol. 112 p1785) and may be obtained as described therein.

Compounds of formula Het-H wherein Het is a group of formula xxxviii above wherein $R_{316}$, $R_{317}$ and $R_{318}$ are each independently hydrogen, $C_{1-4}$ alkyl, nitro, fluoro, chloro, bromo, cyano or formyl may be prepared by methods described in EP-A-0400974 (Merck).

Compounds of formula Het-H wherein Het is a group of formula xxxviii above wherein $R_{317}$ is a group of the formula —$SO_2NR_{320}R_{321}$ may be prepared by reacting a corresponding compound of formula Het-H modified in that $R_{317}$ is a sulphonyl chloride group; with an amine of the formula $HNR_{320}R_{321}$ or a salt thereof; in a solvent inert to the conditions of the reaction.

Compounds of formula Het-H wherein Het is a group of formula xxxviii modified in that $R_{317}$ is a sulphonyl chloride group may be prepared by reacting corresponding compounds of formula Het-H wherein $R_{317}$ is an amino group; with a diazotising agent, such as an alkali metal nitrite, under appropriate conditions (e.g. in the presence of concentrated hydrochloric acid at less than 5° C.); with addition of a source of copper (I) ions (e.g. by addition of cuprous chloride) and sulphur dioxide; in a solvent inert to the conditions of the reaction.

Compounds of formula Het-H wherein Het is a group of formula xxxviii wherein $R_{317}$ is an amino group may be prepared by reducing a corresponding compound wherein $R_{317}$ is a nitro group with a reducing agent, for example hydrogen gas with a catalyst such as a palladium metal catalyst.

Compounds of formula I modified in that $R_{50}$ is a group of formula xxxv, xxxvi, or xxxvii above (i.e. so-called 'pro-drugs') may be prepared by reacting an alkali metal salt of a compound of formula I above wherein $A_{51}$ is oxygen and $R_{50}$ is hydrogen with compounds of structures xxxv, xxxvi or xxxvii above respectively wherein the free valency shown in said structures is attached to halo, suitably chloro in a solvent inert to the conditions of the reaction; preferably in the presence of an alkali metal iodide, for example potassium iodide.

Compounds of formula I wherein $A_{51}$ is oxygen and $R_{50}$ is hydrogen may be prepared by hydrolysis of a compound of formula I wherein $A_{51}$ is oxygen and $R_{50}$ is lower alkyl (prepared as described above), for example, by heating under acid or alkaline conditions.

Alternatively, compounds of formula I wherein $A_{51}$ is oxygen and $R_{50}$ is hydrogen may be prepared by deprotecting compounds of formula I in which $A_{51}$ oxygen modified in that $R_{50}$ represents a protecting group, for example:

1) an aralkyl group, by ether cleavage, for example using hydrobromic acid in a liquid inert to the conditions of the reaction;
2) an aralkyl group (for example benzyl or trityl) for example by hydrogenolysis e.g. with hydrogen over palladium on carbon; or
3) a trialkyl silyl group (for example t-butyldimethylsilyl) by methods of desilylating known to those skilled in the art, for example, by reaction with a source of fluoride, e.g. tetrabutylammonium fluoride).

It will be appreciated by a person skilled in the art that a wide variety of other protecting groups may be used. Examples of such protecting groups and methods for their addition and removal can be found in the textbook "Protective Groups in Organic Synthesis" by T. W. Greene, john Wiley & Sons, 1981.

it will also -be appreciated that reactions described above with respect to compounds wherein $R_{50}$ is $C_{1-4}$ alkyl may also be carried out by use of corresponding compounds modified in that $R_{50}$ is a protecting group as described above.

In a further aspect, therefore, the present invention provides novel intermediate compounds of the formula XC

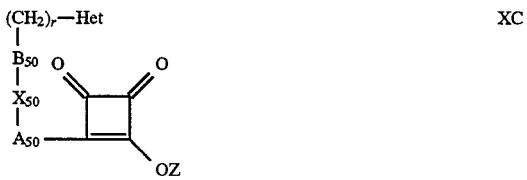

wherein Z is a protecting group of the type described above.

Compounds of formula I wherein $A_{50}$ is sulphur or a group of the formula —$NR_{52}$— may be prepared by reacting a compound of formula XCI

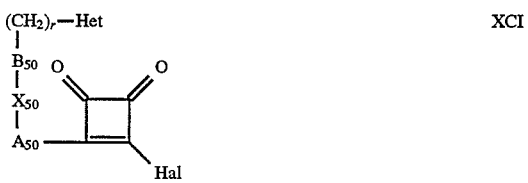

wherein Hal is halo, suitably bromo or chloro; with a compound of the formula $HSR_{50}$ or $HNR_{50}R_{52}$ respectively, (or their alkali metal salts); in a solvent (such as pyridine) inert to the conditions of the reaction. Preferably, where $A_{51}$ is sulphur, this reaction is followed by treatment with a strong acid, such as concentrated hydrochloric acid. Any salt formed may be neutralised, if desired, to provide the corresponding free acid.

Compounds of formula I wherein A is sulphur or a group of formula —$NR_{52}$— and $R_{51}$ is $C_{1-4}$ alkyl may also be prepared by reaction of a compound of formula XCI with hydrogen sulphide or ammonia respectively, followed by treatment with an alkylating agent as required.

Compounds of formula XCI may be prepared by reacting a salt, suitably an alkali metal salt, of a compound of formula I wherein $A_{51}$ is oxygen and $R_{50}$ is hydrogen; with a halogenating agent, suitably a chlorinating agent such as oxalyl chloride; in a solvent inert to the conditions of the reaction.

Compounds of formula I wherein $A_{51}$ is —$NR_{52}$— wherein $R_{52}$ is as defined above may also be prepared by treating a compound of formula I wherein $A_{50}$ is oxygen and $R_{50}$ is $C_{1-4}$ alkyl with a compound of formula $HNR_{50}R_{52}$ or alkali metal salts thereof, in a solvent inert to the conditions of the reaction.

All novel intermediate compounds herein described containing a cyclobutenedione ring are key intermediates in the present invention and form a further aspect of the invention.

Novel intermediates are also provided which correspond to the preferred structures of formula I above (i.e. structures of formulae II, III and IV, modified in that $R_{310}$ is a protecting group as described above).

Salts of compounds of formula I which are also within the scope of this invention may be prepared by conventional means such as by reacting the free acid or free base forms of the compound of formula I with one or more equivalents of the appropriate base or acid.

The therapeutic activity of compounds of formula I has been demonstrated by the following tests. In test A the binding affinity of compounds to the adrenal membrane angiotensin II receptor was determined in vitro and in tests B and C the antihypertensive effect of the compounds was measured in vivo. A detailed description of the tests follows.

Test A

1) Preparation of Membranes

Adrenal glands from male New Zealand white rabbits were homogenised on ice in 20 mM aqueous sodium bicarbonate solution containing 50 µM PMSF (phenylmethanesulphonyl fluoride) (2 ml/g wet weight) using a Polytron (Trademark) homogeniser for 3×15 seconds at setting 8. The homogenate was centrifuged at 900 g for 10 minutes at 4° C. and the pellet was discarded. The supernatant was recentrifuged at 30000 g for 30 minutes at 4° C., and the resulting pellet was resuspended in assay buffer (50 mM Tris-HCl, pH 7.4, containing 1 mM EDTA, 6.5 mM $MgCl_2$, 125 mM NACl, 50 µM PMSF, 5 µg/ml pepstatin and 50 µg/ml each of leupeptin, antipain, aprotinin and chymostatin): 10 ml per g original tissue wet weight. Polyethylene glycol was added (final concentration 30%) as a cryopreservant and the membrane preparation divided into aliquots and stored at −80° C. until required. Protein was determined by a modification of the method of Lowry (Markwell et al, (1978) Anal. Biochem., 87: 206–210).

2) Binding Assay

Aliquots of rabbit adrenal membranes containing 10–30 µg protein were incubated with 0.05 nM [$^{125}$I]angiotensin II in the presence or absence of potential angiotensin II antagonists in 1 ml polyamide tubes in a total volume of 200 µl assay buffer. After incubation for 60 minutes am 25° C. the reaction was terminated by the addition of ice-cold assay buffer, and the bound and free radioactivity was separated through Skatron (Trademark) receptor-binding filters, prewetted with assay buffer, using a Skatron cell harvester. The filters were washed with ice-cold phosphate buffered saline, dried, and the trapped radioactivity was determined using a gamma counter. Non-specific binding, measured in the presence of 2 µM unlabelled angiotensin II, was subtracted from total binding to obtain specific binding. Radioligand binding curves were analysed using EBDA and LIGAND (Cambridge Biosoft). Values for binding affinity were obtained by nonlinear regression analysis of untransformed data.

The activities of the compounds described in the Examples given hereinafter are set out below in Table A, Column 1.

Test B

Female rats, weight range 180–240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the mail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the predose reading, blood pressure was measured at 1.5 and 5.0 hours after dosing. The degree of blood pressure reduction sufficient to achieve a significance level of p<0.01 compared to controls was 9% after correction for control changes at appropriate time intervals. Thus, compounds were considered to be active in this test if they produced a reduction of blood pressure after correction of 9% or greater than 9%.

Threshold antihypertensive doses of compounds of formula I were determined in the following way. Compounds were tested initially at a particular dose level, for example 90 mg/kg. If the compound was considered sufficiently active (giving a reduction of blood pressure equal to or greater than 16% after correction it was retested at a lower dose level, for example 30 mg/kg. By testing at successively lower dose levels, a threshold antihypertensive dose (dose giving a reduction of blood pressure of between 9 and 16% after correction; was determined. Compounds inactive at a particular dose level and giving a reduction of blood pressure equal to or greater than 16% after correction at the next highest dose level were designated as having a threshold antihypertensive dose within the range covered by the two dose levels.

The activities of the compounds described in the Examples given hereinafter are set out below in Table A, Column 2.

Test C

The procedure of Test B above was carried out subject to the modification of pretreating the rats with bendrofluazide 10 mg/kg (an orally administered diuretic) at 16 hours and 2 hours prior to the dose of the test compound, to ensure activation of the reninangiotensin system.

The activities of the compounds described in the Examples given hereinafter are set out below in Table A, Column 3.

The antihypertensive activity of the compounds of the present invention may also be demonstrated in rats in which the renin-angiotensin system has been activated by surgical intervention.

TABLE A

| FINAL PRODUCT OF EXAMPLE | COLUMN 1 (Ki from Test A) ($\times 10^{-9}$ M) | COLUMN 2 (Threshold antihypertensive dose from Test B) (mg/kg) | COLUMN 3 (Threshold antihypertensive dose from Test C) (mg/kg) |
|---|---|---|---|
| 1 | 97.6 | — | 30 |
| 2 | 97.6 | — | 30 |
| 4 | 5 | 0.1 | 0.1 |
| 5 | 1.78 | 1 | 1 |
| 6 | 400 | — | — |
| 8 | 3.19 | 10 | <10 |
| 9 | 3.71 | 10 | 0.1 |
| 11 | 393 | — | — |
| 12 | 13.3 | — | — |
| 13 | 19 | 10 | <10 |
| 15 | 13.5 | — | 3 |
| 16 | 1890 | — | — |
| 17 | 21.5 | — | — |
| 20 | 81.7 | 3 | 1 |
| 22 | 3.68 | — | 30 |
| 24 | 11.1 | — | 3 |
| 28 | 27.7 | — | 10 |
| 29 | 13.7 | >3 | 3 |
| 30 | 77.9 | — | $\leq 10$ |

The invention is illustrated by the following non-imitative Examples in which compositions of mixed solvents are given by volume. Novel compounds were characterised by one or more of the following: elemental analysis, nuclear magnetic resonance and infra-red spectroscopy.

Flash chromatography was performed according to the method of Still et al., J. Org. Chem. (1978), Vol. 43, pp 2923–5.

EXAMPLE 1 a) A mixture of 3-isopropoxy-4-tributylstannyl-cyclobut-3-ene-1,2-dione (4.68 g; preparable as described in Liebeskind and Fengl, Journal of Organic Chemistry (1990), Vol.55, pp 5359/5364), 1-bromo-2-iodobenzene (3.54 g), dry dimethylformamide (15 ml), tetrakis(triphenylphosphine)palladium(0) (0.606 g) and cuprous iodide (0.196 g) was stirred under a nitrogen atmosphere at ambient temperature for approximately 2.5 hours then kept at ambient temperature for 3 days. Diethyl ether (225 ml) was added, and the mixture obtained was washed with saturated aqueous ammonium chloride (225 ml) and then with 10% aqueous potassium fluoride solution (3×225 ml). The organic phase was filtered through a silica bed (5 cm diameter×1 cm depth), and the collected solids were washed with diethyl ether (50 ml). The resulting orange filtrate and washings were combined and evaporated to give a semi-solid brown oil, which was purified by flash chromatography on silica gel (loading in dichloromethane and eluting with 20% diethyl ether in petroleum ether (b.p. 40°–60° C.)) to give the intermediate compound 3-(2-bromophenyl)-4-isopropoxycyclobut-3-ene-1,2-dione, as a yellow oil (2.16 g).

b) The product from Example 1 (a) above (2.16 g) was dissolved in toluene (170 ml) and to this was added 4-methylbenzeneboronic acid (1.94 g), tetrakis-(triphenylphosphine)palladium(0) (0.53 g), ethanol (8.3 ml) and aqueous sodium carbonate solution (2M; 8.3 ml). The resulting mixture was heated under reflux under a nitrogen atmosphere for 3.5 hours. The dark reaction mixture obtained was allowed to cool to ambient temperature then washed with water (2×50 ml). The organic phase was dried over magnesium sulphate, then evaporated to give a brown oil (3.37 g), which was purified by flash chromatography on silica gel (eluting with dichloromethane), to give a yellow oil (1.48 g). Trituration of this oil with 1:1 petroleum ether (b.p. 40°–60° C.):diethyl ether gave a suspension of a yellow solid. The solution was removed and the solid residue obtained was washed with petroleum ether (b.p. 40°–60° C.) and dried in vacuo to give the further intermediate compound 3-isopropoxy-4-(4'-methylbiphenyl-2-yl)cyclobut-3-ene-1,2-dione as a pale yellow solid (0.96 g; m.p. 126°–30° C.).

c) 3-Isopropoxy-4-(4'-methylbiphenyl-2-yl)cyclobut-3-ene-1,2-dione (1.24 g; preparable as described in Example 1(b)), carbon tetrachloride (40 ml), recrystallised N-bromosuccinimide (0.79 g) and AIBN (azobis (isobutyronitrile)) (40 mg) were heated together under reflux for 4.5 hours. Further AIBN (23 mg) was added and reflux was continued for a further 4.5 hours. The mixture was kept at ambient temperature for approximately 16 hours, then cooled briefly ice-water. The resulting yellow supernatant was removed. The off-white solid obtained was washed with cold carbon tetrachloride (approx. 3 ml). The resulting yellow supernatant and washings were combined and evaporated to give a yellow oil which was dried in vacuo to give the further intermediate compound 3-(4'-bromomethylbiphenyl-2-yl)-4-isopropoxy-cyclobut-3-ene-1,2-dione (1.74 g).

d) 2-Ethyl-5,7-dimethyl-3H-imidazo[4,5-b]pyridine (0.66 g; preparable as described in Mantlo et al, J. Med. Chem. 34, (1991), pp 2919/2922 and in EP-A-0400914; Merck), and anhydrous potassium carbonate (1.02 g) were added to a solution of 3-(4'-bromomethylbiphenyl-2-yl)-4-isopropoxycyclobut-3-ene-1,2-dione (1.88 g; preparable as described in Example 1(c)) in dry dimethylformamide (10 ml) and the resulting mixture was stirred at ambient temperature for approximately 16 hours. More 2-ethyl-5,7-dimethyl-3H-imidazo[4,5-b]pyridine (0.33 g) was added to the dark reaction solution obtained, and stirring was continued at ambient temperature for an additional 24 hours. The resulting dark mixture was partitioned between ethyl acetate (100 ml) and water (50 ml). The organic layer was then separated, washed with water (50 ml), and dried over magnesium sulphate. The resulting solution was evaporated to leave a dark oil which was purified by flash chromatography on silica gel (eluting with 1% industrial methylated spirit in dichloromethane) followed by flash chromatography on silica gel (eluting with ethyl acetate) and flash chromatography on silica gel (eluting with 0% rising to 2% methanol in dichloromethane) to give 3-[4'-(2-ethyl-5,7-dimethyl-3H-imidazo[4,5-b]pyrid-3-ylmethyl)biphenyl-2-yl]-4-isopropoxycyclobut-3-ene-1,2-dione, an active compound of the present invention, as a yellow foam (0.176 g) which melted slowly at 60° C. or above.

EXAMPLE 2 a) A mixture of 1,2-diiodobenzene (6.6 g) and tetrakis (triphenylphosphine)palladium(0) (0.34 g) in AR toluene (100 ml) was stirred under a nitrogen atmosphere at ambient temperature. A solution of sodium carbonate (2 g) in water (15 ml) was added. The resulting orange mixture was stirred and heated under reflux while a solution of 4-methylbenzeneboronic acid (1.36 g) in industrial methylated spirit (40 ml) was added dropwise over a period of 40 minutes. The mixture obtained was heated under reflux for an additional 4 hours, then cooled to ambient temperature. Aqueous hydrogen peroxide (30%; 1 ml) was added and the resulting mixture was stirred for 1 hour at ambient temperature. Saturated aqueous sodium chloride solution (50 ml) was then added and the organic phase was separated. The aqueous phase was extracted with ethyl acetate (2×50 ml) and the combined organic phases were washed with saturated aqueous sodium chloride solution (1×70 ml), dried over magnesium sulphate and evaporated to give an orange oil. This oil was triturated with petroleum ether (b.p. 40°–60° C.) (200 ml) to give a gum which was partially purified by flash chromatography on silica gel (eluting with petroleum ether (b.p. 40°–60° C.): ethyl acetate (4:1)) then further purified by high performance liquid chromatography on a silica column (eluting with petroleum ether (b.p. 60°–80° C.) at 200 ml/minute), to give the intermediate compound 2'-iodo-4-methylbiphenyl as a colourless oil (1.3 g).

b) The product from Example 2(a) above (1.23 g) was dissolved in carbon tetrachloride (30 ml). N-bromosuccinimide (0.82 g) was added followed by AIBN (33 mg). The mixture obtained was heated under reflux for 4.5 hours then kept for approximately 16 hours at ambient temperature. The resulting pink supernatant solution was removed, and the residual white solid obtained was triturated with additional carbon tetrachloride (approx. 3 ml). The supernatant and washings from the trituration were combined and then evaporated to give the further intermediate compound 4-(bromomethyl)-2'-iodobiphenyl as a pink/red oil (1.69 g).

c) 2-Ethyl-5,7-dimethyl-3H-imidazo[4,5-b]pyridine (0.731 g) and anhydrous potassium carbonate (1.15 g) were stirred in dry dimethylformamide (10 ml) for 10 minutes. A solution of the product of Example 2(b) (1.65 g) in dry dimethylformamide (10 ml) was added dropwise, over a period of approximately 5 minutes. The resulting suspension was stirred at ambient temperature for approximately 16 hours and then partitioned between diethyl ether (50 ml) and water (50 ml). The layers were separated and the aqueous phase was extracted with more diethyl ether (25 ml). The combined organic phases were then dried over magnesium sulphate and evaporated to give a brown oil. This oil was purified by flash chromatography on silica gel (eluting with ethyl acetate) and then dried in vacuo to give the further intermediate compound 2-ethyl-3-(2'-iodobiphenyl-4-ylmethyl)-5,7-dimethyl-3H-imidazo[4,5-b]pyridine as a brown oil (1.07 g).

d) A portion of the product from Example 2(c) (97 mg) was dissolved in dry dimethyl formamide (1 ml). 3-Isopropoxy-4-tributylstannylcyclobut-3-ene-1,2-dione (91 mg) was added followed by tetrakis (triphenylphosphine)palladium(0) (20 mg) and then cuprous iodide (8 mg). After stirring under a nitrogen atmosphere for 70 minutes, additional tetrakis(triphenylphosphine) palladium(0) (16 mg) and cuprous iodide (9 mg) were added and stirring was continued am ambient temperature for an additional 50 minutes. Additional 3-isopropoxy-4-tributylstannylcyclobut-3-ene-1,2-dione (41 mg) was added and stirring was continued for approximately 72 hours. The solution was then taken into a combined work up (see "f" below).

e) The remainder of the product of Example 2(c) (0.94 g) was dissolved in dry dimethylformamide (4 ml) and the solution obtained was stirred at ambient temperature under a nitrogen atmosphere as 3-isopropoxy-4-tributylstannylcyclobut-3-ene-1,2-dione (1.29 g) followed by tetrakis(triphenylphosphine)palladium(0) (0.143 g) and cuprous iodide (40 mg) were added. The resulting mixture was stirred at ambient temperature for 5.5 hours. Additional tetrakis(triphenylphosphine)palladium(0) (0.14 g) and cuprous iodide (0.12 g) were then added. Stirring was continued under nitrogen for 72 hours and the resulting solution was then taken into the combined work-up (see "f" below).

f) The two red/brown reaction solutions from (d) and (e) above were combined and diluted with diethyl ether (75 ml) and washed with saturated aqueous ammonium chloride (50 ml) then 10% aqueous potassium fluoride solution (3×30 ml) to give a grey solid insoluble material in both phases. The organic phase was filtered through diatomaceous earth (available under the trade name "Celite") and a small aqueous phase was removed. The organic phase was evaporated to give an orange oil which was partially purified by flash chromatography on silica gel (eluting with 0% rising to 4% methanol in dichloromethane). Further purification was effected by flash chromatography on silica gel (eluting with diethyl ether) to give a semi-solid foam which was broken up and dried in vacuo to give 3-[4'-(2-ethyl-5,7-dimethyl-3H-imidazo[4,5-b]pyrid-3-ylmethyl)biphenyl-2-yl)-4-isopropoxycyclobut-3-ene-1,2-dione, an active compound of the present invention, as a yellow solid, (0.42 g), substantially identical to the product of Example 1(d).

EXAMPLE 3 a) To a solution of 1-bromo-2-iodobenzene (200 g) and 4-methylbenzeneboronic acid (105 g) in toluene (11) were added sodium carbonate (164.8 g), industrial methylated spirit (165 ml), water (165 ml) and finally tetrakis(triphenylphosphine)palladium(0) (40.8 g). The mixture obtained was stirred and heated at 95°–100° C. under a nitrogen atmosphere for 18 hours. After cooling to ambient temperature, water (11) was added, and the resulting mixture was stirred for 10 minutes. The organic layer was then separated and dried over magnesium sulphate. The solvent was evaporated under reduced pressure to leave the crude product.

The reaction was repeated as above on 0.45×scale and the crude products of both reactions were combined and stirred with hexane (11) for 30 minutes. Insoluble material was removed by filtration and the solvent was evaporated under reduced pressure. The residue was distilled under reduced pressure through a fractionating column packed with glass helices to give the intermediate compound 2-bromo-4'-methylbiphenyl (241.7 g) as a colourless oil (b.p. 98°–102° C. at 0.8 mmHg).

b) To a solution of 2-bromo-4'-methylbiphenyl (9.0 g; obtainable as described in Example 3 (a) and in Gomberg and Pernert, J. Am. Chem. Soc. (1926) Vol 48 p 1373) in tetrahydrofuran (60 ml) was added butyllithium (2.5M in hexanes, 15.3 ml) dropwise at −70° C. under a nitrogen atmosphere over a period of 3 minutes. The mixture was stirred for 10 minutes at −70° C. then added to a solution of 3,4-diisopropoxycyclobut-3-ene-1,2-dione (7.6 g) in tetrahydrofuran (100 ml) at −70° C. under nitrogen over a period of 1 minute. The solution obtained was stirred for an additional 30 minutes at −70° C. then quenched with trifluoroacetic anhydride (6.4 ml), followed by saturated aqueous ammonium chloride (40 ml). The resulting mixture was allowed to warm to ambient temperature, then partitioned between diethyl ether (300 ml) and aqueous sodium bicarbonate (5%, 300 ml). The aqueous layer was re-extracted with diethyl ether (200 ml) and the combined organic layers were washed with brine, dried over magnesium sulphate, and evaporated to give a yellow oily solid which was purified by flash chromatography on silica gel (eluting with 10% rising to 20% ethyl acetate in petroleum ether (b.p. 60°–80° C.)) to give the intermediate compound 3-isopropoxy-4-(4'-methylbiphenyl-2-yl)cyclobut-3-ene-1,2-dione as a yellow solid (6.7 g), substantially identical to the product of Example 1(b). The above method is described in Reed et al, Journal of Organic Chemistry (1988) Vol.53, p 2477.

It will be appreciated that this intermediate compound may be reacted as described, for example, in Examples 1(c) and 1(d) to provide active compounds of the present invention, such as the active compound of Example 1.

EXAMPLE 4

The final products of Examples 1 and 2 (0.35 g), glacial acetic acid (7.5 ml) and water (7.5 ml) were heated together at 95°–100° C. under a nitrogen atmosphere for 5 hours. The resulting yellow solution was filtered through a cotton wool plug and evaporated to give a glassy brown oil. Trituration of this oil with ethyl acetate (5 ml) gave a yellow solid which was dried in vacuo at 70° C. to provide 3-[4'-(2-ethyl-5,7-dimethyl-3H-imidazo[4,5-b]pyrid-3-ylmethyl)biphenyl-2-yl]-4-hydroxycyclobut-3-ene-1,2-dione, an active compound of the present invention (0.23 g; m.p. 245°–247° C.).

EXAMPLE 5

3-[4'-(2-Ethyl-5,7-dimethyl-3H-imidazo[4,5-b]-pyrid-3-ylmethyl)biphenyl-2-yl]-4-hydroxycyclobut-3-ene-1,2-dione (1.3 g; preparable as described in Example 4) was suspended in distilled water (10 ml) and cooled in an ice bath whilst aqueous sodium hydroxide solution (0.1M; 29 ml) was added dropwise. The resulting mixture was evaporated under reduced pressure (bath temperature 50° C. or below) giving a brown oil which was triturated with diethyl ether (50 ml) to produce a yellow solid. This solid was collected and dried in vacuo at 60° C. Further trituration of the dried solid with diethyl ether (100 ml) and thorough drying in vacuo at 70° C. provided the sodium salt of 3-[4'-(2-ethyl-5,7-dimethyl-3H-imidazo[4,5-b]pyrid-3-ylmethyl)biphenyl-2-yl]-4-hydroxycyclobut-3-ene-1,2-dione (1.18 g), an active compound of the present invention. The compound melted slowly at 180° C. or above.

EXAMPLE 6

3-[4'-(2-Ethyl-5,7-dimethyl-3H-imidazo[4,5-b]pyrid-3-ylmethyl)biphenyl-2-yl)-4-isopropoxycyclobut-3-ene-1,2-dione (0.44 g; preparable as in Example 2) was stirred in saturated ethanolic ammonia solution (10 ml) at ambient temperature for 3 hours and then kept at ambient temperature for approximately 16 hours. The solvent was evaporated and the resulting residue was triturated with diethyl ether to give an off-white solid which was dried in vacuo to give 3-amino-4-[4'-(2-ethyl-5,7-dimethyl -3H-imidazo[4,5-b]pyrid-3-ylmethyl)biphenyl-2-yl]cyclobut-3-ene-1,2-dione (0.25g; m.p. 217° C.), an active compound of the present invention.

EXAMPLE 7

5 7-Dimethyl-2-propyl-3H-imidazo[4,5-b]pyridine (0.69 g) (preparable as described by Mantio et al, J. Med. Chem. 34, (1991), pp 2919/2922 and in EP-A-0400974; Merck) was added to a stirred suspension of sodium hydride (0.15 g; 60% suspension in mineral oil) in dry dimethylformamide (10 ml) over a period of 15 minutes, under a nitrogen atmosphere. Stirring was continued for a further 30 minutes. The resulting solution was added to a stirred solution of 3-(4'-bromomethylbiphenyl-2-yl)-4-isopropoxycyclobut-3-ene-1,2-dione (1.46 g; preparable as in Example 1(c)) in dry dimethylformamide (10 ml) at 0°–5° C. After stirring for 1 hour at 0°–5° C. the dark solution obtained was poured into ethyl acetate (75 ml) and the resulting mixture was washed with water (60 ml). The aqueous phase was then extracted with ethyl acetate (60 ml) and the combined organic phases were washed with water (3×60 ml) and dried over magnesium sulphate. The solvent was removed under reduced pressure and the resulting residue was purified by flash chromatography on silica gel (eluting with ethyl acetate/ petroleum ether (b.p. 40°–60° C.) (4:1)) to give 3-[4'-(5,7-dimethyl-2-propyl-3H-imidazo[4,5-b]pyrid-3-ylmethyl) biphenyl-2-yl]-4-isopropoxycyclobut-3-ene-1,2-dione, an active compound of the present invention, as a yellow gum (0.73 g).

EXAMPLE 8

A solution of the final product of Example 7 (0.73 g) in a mixture of acetic acid (38 ml) and water (17 ml) was stirred at 95°–100° C. under a nitrogen atmosphere for 18 hours. The solvent was removed under reduced pressure and the resulting residue was triturated with ethyl acetate (20 ml) to give 3-[4'-(5 7-dimethyl-2-propyl-3H-imidazo[4,5-b]pyrid-3-ylmethyl)biphenyl-2-yl]-4-hydroxycyclobut-3-ene-1,2-dione, an active compound of the present invention, as a yellow solid (0.44 9; m.p. 240° C., softening from 210° C.).

EXAMPLE 9

The final product of Example 8 (0.40 g) was dissolved in a mixture of aqueous sodium hydroxide solution (2.5M; 15 ml) and industrial methylated spirit (15 ml) and the resulting solution was extracted with dichloromethane (2×15 ml). The combined extracts were dried over magnesium sulphate and the solvent was evaporated to give the sodium salt of 3-[4'-(5,7-dimethyl-2-propyl-3H-imidazo[4,5-b]-pyrid-3-ylmethyl)biphenyl-2-yl]-4-hydroxycyclobut-3-ene-1,2-dione (0.4 g; m.p. 182° C., with slow decomposition), an active compound of the present invention.

EXAMPLE 10 a) 2-Ethyl-5,7-dimethyl-3H-imidazo[4,5-b]pyridine (2.17 g) was added to stirred fuming sulphuric acid (7 ml) and the resulting solution was warmed to 80° C. Potassium nitrate (3.0 g) was added in portions over a period of 10 minutes and the resulting mixture was heated am between 95 and 100° C. for 10 minutes, cooled, then poured onto ice (approx. 25 g). The mixture was neutralised with concentrated aqueous ammonia solution and then extracted with dichloromethane (2×50 ml). The combined extracts were dried over magnesium sulphate and the solvent was then evaporated. Recrystallization of the resulting residue from ethyl acetate (15 ml) gave the intermediate compound 2-ethyl-5,7-dimethyl-6-nitro-3H-imidazo-[4,5-b]pyridine (1.01 g; m.p. 146°–149° C.).

b) A solution of the product of Example 10(a) (1.01 g) in industrial methylated spirit (75 ml) was shaken in an atmosphere of hydrogen in the presence of palladium on carbon (10%; 120 mg) at ambient temperature and pressure for 7 hours. The resulting mixture was filtered through diatomaceous earth (available under the trade name 'Celite') and the filtrate was evaporated to leave a viscous pale brown oil. Trituration of this oil with diethyl ether (30 ml) gave the intermediate compound 6-amino-2-ethyl-5,7-dimethyl-3H-imidazo[4,5-b]pyridine (0.88 g; m.p. 153°–155° C.).

c) 6-Amino-2-ethyl-5,7-dimethyl-3H-imidazo[4,5-b]pyridine (1.89 g; preparable as in Example 10 (b)) was dissolved with stirring in a mixture of concentrated hydrochloric acid (2.6 ml) and water (2.6 ml) and cooled to below 5° C. A solution of sodium nitrite (0.76 g) in water (2.2 ml) was then added dropwise, keeping the temperature below 5° C., to give a solution (A).

Cuprous chloride (0.26 g) was dissolved in a saturated solution of sulphur dioxide in acetic acid (10 ml) and the resulting solution (B) was cooled to 10° C. Solution (A) was then added to the stirred cooled solution (B) at 0°–10° C., in portions, over a period of 10 minutes. The resulting mixture was stirred for 3.5 hours at 10°–15° C., added to ice (100 g) and then extracted with dichloromethane (3×50 ml). The combined extracts were dried over magnesium sulphate and the solvent was evaporated to give a pale yellow solid which was added to aqueous dimethylamine solution (30%; 20 ml) at ambient temperature. The resulting mixture was stirred for 30 minutes. The solvent was then evaporated under reduced pressure and the residue obtained was triturated with water (5 ml) to give the intermediate compound 2-ethyl-5,7, N,N-tetramethyl-3H-imidazo[4,5-b]pyridine-6-sulphonamide (0.21 g; m.p. 179°–182° C.).

d) Sodium hydride (60% dispersion in mineral oil; 25 mg) was added to a solution of the product of Example 10(c) (0.19 g) in dry dimethyl formamide (2 ml) under a nitrogen atmosphere and the resulting mixture was stirred for 10 minutes. The solution obtained was added dropwise by syringe at 0°–5° C. to a stirred solution of 3-(4'-bromomethylbiphenyl- 2-yl)-4 isopropoxycyclobut-3-ene-1, 2-dione (0.289 g; preparable as in Example 1 (c)) in dry dimethylformamide (2 ml). The resulting mixture was stirred for 1.5 hours at ambient temperature, poured into ethyl acetate (50 ml), and then washed with water (2×25 ml). The aqueous washings were then extracted with ethyl acetate (40 ml). The combined organic solutions were dried over magnesium sulphate and the solvent was evaporated under reduced pressure. The resulting residue was purified by flash chromatography on silica gel (eluting with ethyl acetate/petroleum ether (b.p. 40°–60° C.) (4:1)) to give 2-ethyl-3-[2'-(2-isopropoxy-3,4-dioxocyclobut-1-en-1-yl) biphenyl-4-ylmethyl]-5,7,N,N-tetramethyl-3H-imidazo[4,5-b]pyridine-6-sulphonamide (0.2 g; m.p. 80° C., with slow decomposition), an active compound of the present invention.

EXAMPLE 11

A solution of the final product of Example 10 (0.19 g) in a mixture of acetic acid (8.3 ml) and water (3.7 mi) was heated at 95°–100° C. for 15 hours. The solvent was removed by evaporation under reduced pressure and the resulting residue was triturated with ethyl acetate (5 ml). The solid obtained was collected and dried in vacuo at 70° C. to give 2-ethyl-3-[2'-(2-hydroxy-3,4-dioxocyclobut-1-en-1-yl) biphenyl-4-ylmethyl]-5,7, N,N-tetramethyl-3H-imidazo[4, 5-b]pyridine-6-sulphonamide mono-ethyl acetate solvate (0.15 g; m.p. 195°–197° C. (with decomposition)), an active compound of the present invention.

EXAMPLE 12 a) 6-Amino-2-ethyl-5,7-dimethyl-3H-imidazo[4,5-b]-pyridine (0.85 g; preparable as in Example 10(b)) was dissolved with stirring in a mixture of concentrated hydrochloric acid (1.15 ml) and water (1.15 ml) and the resulting solution was cooled to 0° C. A solution of sodium nitrite (0.34 g) in water (1 ml) was added, dropwise, keeping the internal temperature below 5° C. The resulting solution was stirred at this temperature for 10 minutes and then added to a stirred solution of cuprous chloride (0.48 g) in concentrated hydrochloric acid (t.7 ml) keeping the temperature below 10° C. The mixture obtained was stirred at 70° C. for 2 hours and then cooled to ambient temperature. A precipitate was collected and washed with water (5 ml). Recrystallisation of this precipitate from methanol (7.5 ml) gave the intermediate compound 6-chloro-2-ethyl-5,7-dimethyl-3H-imidazo[4,5-b]pyridine hydrochloride (0.21 g; m.p. 284°–287° C. with decomposition). When left for 18 hours the reaction mixture yielded a further quantity of precipitate, which was collected by filtration and recrystallised from methanol to give a second crop (70 mg) of the intermediate compound identified above.

b) Sodium hydride (60% dispersion in mineral oil; 91 rag) was added to a suspension of the product of Example 12(a) (0.28 g) in dry dimethylformamide (4 ml) and the resulting mixture was stirred at ambient temperature under a nitrogen atmosphere for 30 minutes. The mixture obtained was then added dropwise at ambient temperature to a solution of 3-(4'-bromomethylbiphenyl-2-yl)-4-isopropoxycyclobut-3-ene-1,2-dione (0.548 g; preparable as described in Example 1(c)) in dry dimethylformamide (5 ml). The resulting mixture was stirred at ambient temperature for 5 hours and then poured into ethyl acetate (70 ml). The resulting mixture was washed with water (2×25 ml) and the aqueous washings were extracted with ethyl acetate (20 ml). The combined organic phases were dried over magnesium sulphate and the solvent was evaporated under reduced pressure to give the intermediate compound 3-[4'-(6-chloro-2-ethyl-5,7-dimethyl-3H-imidazo[4,5-b]pyrid-3-ylmethyl) biphenyl-2-yl]-4-isopropoxycyclobut-3-ene-1,2-dione as a viscous oil (0.65 g).

c) The product of Example 12(b) (0.65 g) was heated for 18 hours am 95°–100° C. in a mixture of acetic acid (7 ml and water (2.5 ml) under a nitrogen atmosphere. The solvents were evaporated under reduced pressure and the resulting residue was triturated with ethyl acetate (20 ml) to leave a gum. Aqueous sodium hydroxide solution (2.5M; 5 ml) was added to the gum. The resulting suspension was acidified with concentrated hydrochloric acid to give a yellow solid which was collected by filtration and purified by flash chromatography on silica gel (eluting with ethyl acetate/industrial methylated spirit (7:3)) to give 3-[4'-(6-chloro-2-ethyl-5,7-dimethyl -3H-imidazo-[4,5-b]pyrid-3-ylmethyl)biphenyl-2-yl]-4-hydroxy-cyclobut-3-ene-1,2-dione hydrochloride, an active compound of the present invention, as a yellow solid (70 mg; m.p. 205° C. with decomposition).

EXAMPLE 13

Chloromethyl pivalate (3.22 g) was added, dropwise, at ambient temperature, to a stirring suspension of 3-[4'-(2-ethyl-5,7-dimethyl-3H-imidazo[4,5-b]pyrid-3-ylmethyl) biphenyl -2-yl]-4-hydroxycyclobut-3-ene-1,2-dione (4.21 g; preparable as in Example 4) in dry N,N-dimethylacetamide (40 ml). Potassium iodide (2.5 g) was added to the resulting mixture and stirring was continued am ambient temperature for 2 days. More chloromethyl pivalate (3.7 g) was added and stirring was continued for an additional 2 days. The mixture obtained was poured into diethyl ether (500 ml) to give a gum which was separated and then dissolved in a mixture of acetone (100 ml) and ethyl acetate (300 ml). The resulting solution was washed with saturated aqueous sodium bicarbonate solution (2×400 ml) then water (2×400 ml) and dried over magnesium sulphate. The solvents were evaporated under reduced pressure and the residue obtained was purified by flash chromatography on silica gel (eluting with ethyl acetate) to give 2-[4'-(2-ethyl-5,7-dimethyl-3H-imidazo[4,5-b]pyrid-3-ylmethyl)biphenyl-2-yl]-3,4-dioxocyclobut-1-en-1-yloxymethyl pivalate, an active compound of the present invention, as a fellow foam (0.54 g) which melted slowly at 60°–80° C.

EXAMPLE 14

To a stirred solution of 4-ethyl-2-propyl-1H-imidazole-5-carboxaldehyde (0.15 g; preparable as described in WO92/00977; Dupont) in dry dimethylformamide (3 ml) was added sodium hydride (60% dispersion in mineral oil; 36 mg) and stirring was continued for approximately 45 minutes. The resulting solution was then added via canula to a stirred solution of 3-(4'-bromomethylbiphenyl-2-yl)-4-isopropoxycyclobut-3-ene-1,2-dione (0.35 g; preparable as in Example 1(c)) in dry dimethylformamide (3 ml). After stirring for 1 hour, 2-propanol (0.1 ml) was added. The mixture obtained was poured into ethyl acetate (20 ml) then washed with water (15 ml). The aqueous washings were extracted with ethyl acetate (10 ml) and the combined organic phases were washed with water (5×15 ml) and dried over magnesium sulphate. The solvent was removed under reduced pressure and the residue obtained was purified by flash chromatography on silica gel (eluting with ethyl acetate/petroleum ether (b.p. 60°–80° C.) (75:25)) to give 4-ethyl-1-[2'-(3,4-dioxo-2-isopropoxycyclobut-1-en-1-yl) biphenyl-4-ylmethyl]-2-propyl-1H-imidazole-5-carboxaldehyde, an active compound of the present invention, as a foam (0.194 g).

EXAMPLE 15

The product of Example 14 (0.19 g), acetic acid (2 ml) and water (2 ml) were heated together at 95°–100° C. for approximately 5 hours under a nitrogen atmosphere then left at ambient temperature for approximately 17 hours. The solvents were removed under reduced pressure and the resulting residue was triturated with ethyl acetate (2×15 ml) and then dried in vacuo at 80° C. to give 4-ethyl-1-[2'-(2-hydroxy-3,4-dioxocyclobut-1-en-1-yl)biphenyl-4-yl methyl]-2-propyl-1H-imidazole-5-carboxaldehyde, an active compound of the present invention, as a yellow solid (0.12 g; m.p. 241°–245° C.).

EXAMPLE 16

The final product of Example 5 (0.463 g; dried before use by heating in vacuo as the compound appeared to be hygroscopic) was dissolved in dry dimethylformamide (3 ml). To the resulting solution was added a solution of chloromethyl pivalate (0.19 g) in dry dimethylformamide (3 ml). After stirring the resulting mixture for approximately 17 hours, potassium iodide (21 mg) was added and stirring was continued for approximately 3 days. More chloromethyl pivalate (98 mg) was added and stirring was continued for a further 4 days. The solution obtained was then partitioned between water (25 ml) and diethyl ether (25 ml). The aqueous layer was separated and extracted with diethyl ether (2×25 ml). The combined organic layers were dried over magnesium sulphate, the solvent was distilled off and the resulting residue was then purified by flash chromatography on silica gel (eluting with ethyl acetate followed by ethyl acetate/industrial methylated spirit (9:1)). The fractions containing the slower running of the two main products were combined and evaporated under reduced pressure. The resulting residue was triturated with diethyl ether (2 ml) to give a solid which was collected and washed with diethyl ether (1 ml) and then dried to give 3-dimethylamino-4-[4'-(2 -ethyl-5,7-dimethyl-3H-imidazo-[4,5-b]pyrid-3-ylmethyl)

biphenyl-2-yl]cyclobut-3-ene-1,2-dione, an active compound of the present invention, as a colourless solid (34 mg; m.p. 140°–142° C.).

EXAMPLE 17

The final product of Example 4 (1.01 g; dried before use by heating in vacuo as the compound appeared to be hygroscopic) was suspended in dry. N,N-dimethylacetamide (10 ml). The resulting suspension was stirred whilst 1-chloroethyl pivalate (0.90 g; preparable as described in J. Med. Chem. (1978), Vol. 21, p 753) followed by potassium iodide (0.77 g) were added. Stirring was continued at ambient temperature for approximately 3 days. The suspension obtained was then diluted with ethyl acetate (50 ml) and washed with aqueous sodium bicarbonate solution (5%; 50 ml) and then water (4×50 ml). The organic layer was dried over magnesium sulphate, the organic solvents were removed under reduced pressure and the resulting residue was purified by flash chromatography on silica gel (eluting with ethyl acetate) to give 1-[2-[4'-(2-ethyl-5,7-dimethyl-3H-imidazo[4,5-b]pyrid-3-ylmethyl)biphenyl-2-yl]-3,4-dioxocyclobut-1-en-1-yloxy]ethyl pivalate 0.22 ethyl acetate solvate (0.55g), an active compound of the present invention, as a yellow foam which softened and slowly melted at and above 80° C.

EXAMPLE 18 a) A solution of 4-bromomethyl-2'-iodobiphenyl (4.0 g; preparable as in Example 2(b)) and butylamine (40 ml) in dry tetrahydrofuran (55 ml) was stirred for 18 hours an ambient temperature then boiled under reflux for 45 minutes. The solvent was evaporated under reduced pressure and the resulting residue was then dissolved in dichloromethane (100 ml) to give a solution which was washed with aqueous potassium hydroxide solution (1M; 2×50 ml), water (50 ml), then hydrochloric acid (5M; 2×50 ml), then organic layer was dried over magnesium sulphate and the organic solvent was evaporated. The residue obtained was purified by flash chromatography on silica gel (eluting with dichloromethane/methanol (9:1) to give the intermediate compound N-(2'-iodobiphenyl-4ylmethyl)butylamine (1.9 g; m.p. 134°–136° C.).

b) A solution of ethyl 4-chloropyrimidine-5-carboxylate (0.9 g; preparable as described in Bredereck et al., Chem. Ber. (1962), Vol. 95, p 803) in dry tetrahydrofuran (2 ml) was added to a solution of the product of Example 18(a) (1.9 g) and triethylamine (2.5 ml) in dry tetrahydrofuran (10 ml) and the resulting mixture was stirred at ambient temperature for approximately 1.5 hours. The solvent was evaporated under reduced pressure to give a residue which was dissolved in dichloromethane (50 ml), washed with saturated aqueous sodium bicarbonate solution (2×25 ml), and then dried over magnesium sulphate. The solvent was evaporated and the residue obtained was purified by flash chromatography on silica gel (eluting with ethyl acetate) to give the intermediate compound ethyl 4-[N-butyl-N-(2'-iodobiphenyl-4-ylmethyl)amino]pyrimidine-5-carboxylate as a viscous oil (1.5 g).

c) 3-Isopropoxy-4-tributylstannylcyclobut-3-ene-1,2-dione (1.626 g), tetrakis(triphenylphosphine)palladium(0) (0.348 g), cuprous iodide (0.138 g) and the product from Example 18(b) (1.3 g) were stirred together in dry dimethylformamide (20 ml) at ambient temperature under a nitrogen atmosphere for 23.5 hours. After dilution with ether (100 ml) the mixture was washed with saturated aqueous ammonium chloride solution (2×25 ml), aqueous potassium fluoride solution (10%; 2×25 ml) and water (2×25 ml). The organic phase was dried over magnesium sulphate and the solvent was evaporated under reduced pressure to leave a brown solid. This solid was purified by flash chromatography on silica gel (eluting with petroleum ether (b.p. 40°–60° C.)/ethyl acetate (1:1)) to give ethyl 4-[N-butyl-N-[2'-(2-isopropoxy-3,4-dioxo-cyclobut-1-en-1-yl)biphenyl-4-ylmethyl]amino]-pyrimidine-5-carboxylate, an active compound of the present invention, as a yellow oil (0.77 g).

EXAMPLE 19

The product of Example 18(c) (0.67 g) was heated in a mixture of acetic acid (30 ml) and water (15 ml) at 95°–100° C. under a nitrogen atmosphere for 22 hours. The resulting solution was cooled and filtered. The solvents were then evaporated under reduced pressure to give ethyl 4-[N-butyl-N-[2'-(2-hydroxy-3,4-dioxocyclobut-1-en-1-yl)biphenyl-4-ylmethyl]amino]pyrimidine-5-carboxylate, an active compound of the present invention, as a brown solid (0.59 g; m.p. 95° C. (dec)).

EXAMPLE 20

A solution of the final product of Example 19 (0.59 g) and sodium hydroxide (0.51 g) in a mixture of methanol (20 ml) and water (6 ml) was stirred for 7 hours at ambient temperature. The stirred solution was kept for 18 hours at ambient temperature and then acidified to Ph 2 by addition of concentrated hydrochloric acid. The resulting mixture was diluted with water (20 ml) and filtered to give a solid product (400 mg). This solid was then stirred in a solution of sodium hydroxide (0.5 g) in water (10 ml) for 6 hours at ambient temperature and the resulting mixture was acidified to Ph 2 with concentrated hydrochloric acid to give a pale brown precipitate This precipitate was collected and dried to give 4-[N-butyl-N-[2'-(2-hydroxy-3,4 -dioxocyclobut-1-en-1-yl)biphenyl-4-ylmethyl]amino]pyrimidine- 5-carboxylic acid 0.6 hydrochloride (0.2 g; m.p. 172°–175° C. (dec)), an active compound of the present invention.

EXAMPLE 21

Sodium hydride (60% dispersion in mineral oil; 0. 804 g) was added in portions over a period of 15 minutes at ambient temperature to a stirred solution of 2-butyl-2-imidazoline-4-spirocyclopentan-5(1H)-one (3.9 g; preparable as described in WO 91/14679; Sanofi) in dry dimethylformamide (68.5 ml) under a nitrogen atmosphere. Stirring was continued for 45 minutes. The resulting solution was then added co a stirred solution of 3-(4'-bromomethylbiphenyl-2-yl)-4-isopropoxycyclobut-3-ene-1,2-dione (11.17 g; preparable as described in Example 1 (c)) in dry dimethylformamide (68.5 ml) and stirring was continued for 2 hours. 2-Propanol (2.6 ml) was added and the resulting mixture was poured onto ethyl acetate (450 ml) and then washed with water (250 ml). The aqueous layer was separated and extracted with ethyl acetate (300 ml). The combined organic phases were washed with brine (5×200 ml) and then dried over magnesium sulphate. The organic solvent was evaporated under reduced pressure and the resulting residue was purified by flash chromatography on silica gel (eluting with ethyl acetate/petroleum ether (b.p. 60°–80° C.) (7:3)) to give 3-[4'-(2-butyl-5-oxo-2-imidazoline-4-spirocyclopent-1-ylmethyl)biphenyl-2-yl]-4-isopropoxycyclobut-3-ene-1,2-dione, an active compound of the present invention, as a yellow gum (3.6 g).

EXAMPLE 22

A mixture of the product of Example 21 (3.6 g), acetic acid (35.2 ml) and water (35.2 ml) was heated at 95°–100° C. under a nitrogen atmosphere for approximately 4.5 hours. The solvents were evaporated under reduced pressure to leave a gum which was triturated with ethyl acetate (2×90 ml) and then dried in vacuo at 60° C. to give 3-[4'-(2-butyl-5-oxo-2-imidazoline-4-spirocyclopent-1-ylmethyl) biphenyl-2-yl]-4-hydroxycyclobut-3-ene-1,2-dione (1.91 g; m.p. 197°–199° C.), an active compound of the present invention.

EXAMPLE 23 a) A solution of 4-(bromomethyl)-2'-iodobiphenyl (9.23 g; preparable as described in Example 2(b)) in dry dimethylformamide (50 ml) was added to a stirring mixture of 2-butyl-4-chloro-1H-imidazole-5-carboxaldehyde (preparable as described in Drugs of the Future (1991), Vol. 16, p 305), anhydrous potassium carbonate (6.9 g) and dry dimethylformamide (100 ml), at ambient temperature. Stirring was continued at ambient temperature for 24 hours. Water (200 ml) was added and the resulting mixture was extracted with diethyl ether (500 ml then 200 ml). The combined extracts were washed with water (2×100 ml) and dried over magnesium sulphate. The organic solvent was evaporated and the residual orange oil was purified by flash chromatography on silica gel (eluting with 5% then 30% ethyl acetate in petroleum ether (b.p. 60°–80° C.)) to give the intermediate compound 2-butyl-4-chloro-1-(2'-iodobiphenyl-4-ylmethyl)-1H-imidazol-5-carboxaldehyde as a yellow oil (8.06 g).

b) 3-Isopropoxy-4-tributylstannylcyclobut-3-ene-1,2-dione (0.67 g; preparable as described in Liebeskind & Fengl, journal of Organic Chemistry (1990), Vol. 55, pp 5359/5364)), tetrakis(triphenylphosphine)palladium(0) (0.145 g) and cuprous iodide (48 mg) were added to a solution of the product of Example 23(a) (0.5 g) in dry dimethylformamide (5 ml) and the mixture obtained was stirred under a nitrogen atmosphere at ambient temperature for 24 hours. Diethyl ether (50 ml) was added and the resulting mixture was washed with saturated aqueous ammonium chloride (35 ml) then aqueous potassium fluoride solution (10%; 3×20 ml) and the organic solution was dried over magnesium sulphate. The organic solvents were evaporated in vacuo and the residual orange/brown oil was purified by flash chromatography on silica gel (eluting with 20% ethyl acetate in petroleum ether (b.p. 60°–80° C.)) to give 2-butyl-4-chloro-1-[2'-(2-isopropoxy-3,4-dioxocyclobut-1-en-1-yl)biphenyl-4-ylmethyl]-1H-imidazole-5-carboxaldehyde, an active compound of the present invention, as a partially solidified yellow oil (0.22 g).

EXAMPLE 24

A solution of the final product of Example 23 (0.20 g) in a mixture of glacial acetic acid (5 ml) and water (5 ml) was heated at 95°–100° C. for 4.5 hours. More glacial acetic acid (2 ml) and water (2 ml) were added and heating was continued for a further 5 hours. The resulting solution was then cooled to ambient temperature and filtered. The solvents were then evaporated in vacuo to give 2-butyl-4-chloro-1-[2'-(2-hydroxy-3,4-dioxocyclobut-1-en-1-yl) biphenyl-4-ylmethyl]-1H-imidazole-5-carboxaldehyde, an active compound of the present invention, as a yellow solid (0.16 g) which softened and melted at or above 50° C.

EXAMPLE 25 a) Sodium borohydride (39 mg) was added at ambient temperature to a solution of the product of Example 23(a) (0.5 g) in methanol (5 ml) and the resulting solution was stirred for 1.5 hours. The solvent was evaporated in vacuo and water (50 ml) was added to the resulting residue. The mixture obtained was extracted with ethyl acetate (2×50 ml) and the combined extracts w(re dried over magnesium sulphate. The solvent was evaporated in vacuo to give the intermediate compound 2-butyl-4-chloro-5-hydroxymethyl-1-[2'-iodobiphenyl-4-ylmethyl]-1H-imidazole as a yellow oil (0.33 g).

b) 3-Isopropoxy-4-tributylstannylcyclobut-3-ene-1,2-dione (0.402 g), tetrakis(triphenylphosphine)palladium(0) (86 mg) and cuprous iodide (28 mg) were added to a solution of the product from Example 25(a) above (0.30 g) in dry dimethylformamide (5 ml) at ambient temperature under a nitrogen atmosphere. The mixture obtained was stirred for 40 hours. Diethyl ether (50 ml) was added and the resulting mixture was washed with saturated aqueous ammonium chloride solution (30 ml) then aqueous potassium fluoride solution (10%; 2×20 ml). The organic solution was dried over magnesium sulphate and the solvents were evaporated in vacuo. The residual orange oil was dissolved in ethyl acetate (10 ml). Insoluble material was removed by filtration and the solvent was evaporated in vacuo. The residue obtained was then dissolved in diethyl ether (10 ml), insoluble material was again removed by filtration and the solvent was again evaporated in vacuo. The residue obtained was purified by flash chromatography on silica gel (eluting with ethyl acetate/petroleum ether (b.p. 60°–80° C.) (1:1)) to give 3-[4'-(2-butyl-4-chloro-5 -hydroxymethyl-1H-imidazol-1-ylmethyl)biphenyl-2-yl]-4-isopropoxycyclobut-3-ene-1,2-dione, an active compound of the present invention, as a yellow oil (80 mg).

EXAMPLE 26

Methyl 2-butyl-4-chloro-1H-imidazole-5-carboxylate (0.19 g) was added to a stirring suspension of sodium hydride (60% dispersion in mineral oil; 35 mg) in dry dimethylformamide (2 ml) at ambient temperature under a nitrogen atmosphere and stirring was continued for 30 minutes. A solution of 3-(4'-bromomethylbiphenyl-2-yl)-4-isopropoxycyclobut-3-ene-1,2-dione (0.64 g; preparable as in Example 1(c)) in dry dimethyl formamide (3 ml) was added and stirring was continued for 24 hours. The reaction mixture was partitioned between water (20 ml) and diethyl ether (20 ml), and the aqueous layer was separated and extracted with diethyl ether (20 ml). The combined ether solutions were dried over magnesium sulphate and the solvent was evaporated in vacuo. The residue obtained was purified by flash chromatography on silica gel (eluting with 20% ethyl acetate in petroleum ether (b.p. 40°–60° C.)) to give methyl 2-butyl-4-chloro-1-[2'-(2-isopropoxy-3,4-dioxocyclobut-1-en-1-yl)biphenyl-4-ylmethyl]-1H-imidazole-5-carboxylate, an active compound of the present invention, as a yellow oil (0.17 g).

EXAMPLE 27 a) A solution of the product of Example 23(a) (0.5 g) in t-butanol (18.75 ml) was added to a solution of sodium chlorite (1.02 g) and sodium dihydrogen phosphate (1.02 g) in water (24 ml) at ambient temperature and the resulting mixture was stirred vigorously for 40 hours. Sodium metabisulphite was added until the yellow colour of the solution was discharged, then most of the solvents were evaporated in vacuo. Water (75 ml) was added to the resulting residue and the mixture obtained was extracted with dichloromethane (2×50 ml). The combined extracts were dried over magnesium sulphate and the organic solvent was evaporated in vacuo. Trituration of the resulting residue with diethyl ether (5 ml) gave the intermediate compound 2-butyl-4-chloro-1-(2'-iodobiphenyl-4-ylmethyl)-1H-imidazole-5-carboxylic acid as a colourless solid (0.27 g; m.p. 175° C.).

b) 2-Butyl-4-chloro-1-(2'-iodobiphenyl-4-ylmethyl)-11H-imidazole-5-carboxylic acid (0.43 g; preparable as described in Example 27(a)) was added to a stirring suspension of sodium hydride (60% dispersion in mineral oil; 41 mg) in dry dimethylformamide (5 ml) at ambient temperature under a nitrogen atmosphere, and stirring was continued for 30 minutes. Iodomethane (0.06 ml) was added and stirring was continued for 2 hours. Diethyl ether (20 ml) was added and the mixture obtained was washed with water (20 ml). The aqueous washings were extracted with diethyl ether (2×20 ml) and the combined organic phases were dried over magnesium sulphate. The organic solvent was then evaporated to give the further intermediate compound methyl 2-butyl-4-chloro-1-(2'-iodobiphenyl-4-ylmethyl)-1-imidazole-5-carboxylate as an oil (0.43 g).

c) 3-Isopropoxy-4-tributylstannylcyclobut-3-ene-1,2-dione (0.53 g), tetrakis(triphenylphosphine)palladium(0) (0.12 g), and cuprous iodide (38 mg) were added to a solution of the product of Example 27(b) (0.42 g) in dry dimethylformamide at ambient temperature under a nitrogen atmosphere. The mixture was stirred for 18 hours. Diethyl ether (30 ml) was added and the resulting mixture was washed with saturated aqueous ammonium chloride solution (20 ml) followed by aqueous potassium fluoride solution (10%; 2×20 ml). The organic phase was dried over magnesium sulphate and the solvent was evaporated in vacuo. The residue obtained was purified by flash chromatography on silica gel (eluting with 20% rising to 50% ethyl acetate in petroleum ether (b.p. 40°–60° C.)) to give methyl 2-butyl-4-chloro-1-[2'-(2-isopropoxy-3,4-dioxo-cyclobut-1-en-1-yl)biphenyl-4-ylmethyl]-1H-imidazole-5-carboxylate, an active compound of the present invention (substantially identical to the product of Example 26), as a yellow oil (0.1 g).

EXAMPLE 28

Methyl 2-butyl-4-chloro-1-[2'-(2-isopropoxy-3,4-dioxocyclobut-1-en-1-yl)biphenyl-4-ylmethyl]-1H-imidazole-5-carboxylate (0.26 g; preparable as described in Example 27(c)) was heated in a mixture of glacial acetic acid (5 ml) and water (5 ml) at 95°–100° C. for 5 hours. The solvents were evaporated in vacuo and the residue obtained was purified by flash chromatography on silica gel (eluting with 10% rising to 30% industrial methylated spirit in ethyl acetate) to give methyl 2-butyl-4-chloro-1-[2'-(2-hydroxy-3,4-dioxo-cyclobut-1-en-1-yl)biphenyl-4-ylmethyl]-1H-imidazole-5-carboxylate, an active compound of the present invention, as a yellow oil (0.1 g).

EXAMPLE 29

Aqueous sodium hydroxide solution (2M; 1 ml) was added to a solution of the product of Example 28 (90 mg) in methanol (3 ml) at ambient temperature. The resulting mixture was then stirred for 2 hours. The solvent was removed by evaporation in vacuo, and water (2 ml) was added to the residue obtained, followed by sufficient hydrochloric acid (5M) to adjust the resulting solution to pH 1. The resulting yellow precipitate was filtered, washed with water and dried to give 2-butyl-4-chloro-1-[2'-(2-hydroxy-3,4-dioxocyclobut-1-en-1-yl)biphenyl-4-ylmethyl]-1H-imidazole-5-carboxylic acid 0.4 hydrochloride, an active compound of the present invention, as a pale yellow solid (70 mg; m.p. 168° C.).

EXAMPLE 30 a) A mixture of 2-butyl-4-chloro-1H-imidazole-5-carboxaldehyde (4.0 g; preparable as described in Drugs of the Future (1991), Vol. 16, p 305), potassium carbonate (2.94 g) and dry dimethylformamide (50 ml) was stirred for 15 minutes at ambient temperature. 4-Iodobenzyl bromide (6.34 g) was added to the resulting mixture and stirring was continued for approximately 17 hours. The solvent was then evaporated under reduced pressure at 80° C. Water (200 ml) was added to the resulting residue which was then extracted with diethyl ether (2×100 ml). The combined extracts were washed with water (50 ml) and dried over magnesium sulphate. The solvent was evaporated. The resulting residue was purified by flash chromatography on silica gel (eluting with dichloromethane/methanol (80:1)) to give the intermediate compound 2-butyl-4-chloro-1-(4-iodobenzyl)-1H-imidazole-5-carboxaldehyde as an oil (6.9 g).

b) A solution of methyl 3-phenylpropanoate (4.03 g) in dry tetrahydrofuran (50 ml) was added over 15 minutes to a stirred solution of lithium diisopropylamide tetrahydrofuran adduct (16.4 ml; 1.5M solution in cyclohexane) in dry tetrahydrofuran (50 ml) at −70° C. under a nitrogen atmosphere. Stirring was continued at −70° C. for approximately 1 hour. A solution of the product from Example 30(a) (6.6 g) in dry tetrahydrofuran (50 ml) was then added over 15 minutes and the resulting mixture was stirred at −70° C. for 4 hours. The mixture was allowed to warm to 0° C. and was then poured into saturated aqueous ammonium chloride solution (250 ml) and extracted with ethyl acetate (3×150 ml). The combined extracts were washed with brine (50 ml), dried over sodium sulphate and evaporated to dryness under reduced pressure. The resulting residue was triturated with petroleum ether (b.p. 60°–80° C.; 2×100 ml) then further purified by flash chromatography on silica gel (eluting with dichloromethane/methanol (50:1)) to give the intermediate compound methyl 2-benzyl-3-[2-butyl-4-chloro-1-(4-iodobenzyl)-1H-imidazol-5-yl]-3-hydroxypropanoate (5.7 g; m.p. 155°–159° C.) as a solid mixture of diastereoisomers.

c) A solution of the product of Example 30(b) (5.7 g), acetic anhydride (11 ml) and 4-dimethylaminopyridine (0.5 g) in dichloromethane (250 ml) was stirred at ambient temperature for approximately 17 hours and then washed with saturated aqueous sodium bicarbonate solution (2×300 ml). The organic layer was dried over magnesium sulphate and the solvent was evaporated. The resulting residue was dissolved in dry toluene (300 ml) and 1,8-diazabicyclo [5.4.0]undec-7-ene (6 ml) was added. The resulting mixture was heated under nitrogen at 95°–100° C. for approximately 8 hours and cooled. The solvent was then evaporated under reduced pressure, and the resulting residue was purified by flash chromatography on silica gel (eluting with dichloromethane/methanol (60:1)) to give the intermediate compound (E)-methyl 2-benzyl-3-[2-butyl-4-chloro-1-(4-iodobenzyl)-1H-imidazol-5-yl]propenoate as an oil (3.5 g).

d) A mixture of the product of Example 30 (c) (0.8 g), 3-isopropoxy-4-tributylstannylcyclobut-3-ene-1,2-dione (0.9 g), tetrakis(triphenylphosphine)palladium(0) (0.2 g), cuprous iodide (0.1 g) and dry dimethylformamide (5 ml) was stirred at ambient temperature under a nitrogen atmosphere for approximately 17 hours. The solvent was evaporated under reduced pressure and the resulting residue was dissolved in diethyl ether (150 ml). The solution obtained was washed with saturated aqueous ammonium chloride solution (50 ml), then with saturated aqueous potassium fluoride solution (2×50 ml) and then dried over magnesium sulphate. The solvent was evaporated and the residue obtained was purified by flash chromatography on silica gel (eluting with dichloromethane/methanol (50:1)) to give the intermediate compound (E)-methyl 2-benzyl-3-[2-butyl-4-chloro-1-[4-(2-isopropoxy-3,4-dioxocyclobut-1-en-1-yl) benzyl]-1H-imidazol-5-yl]propenoate as an oil (0.4 g).

e) A mixture of (E)-methyl 2-benzyl-3-[2-butyl-4-chloro-1-[4-(2-isopropoxy-3,4-dioxocyclobut-1-en-1-yl)benzyl]-1H-imidazol-5-yl ]propenoate (1.2 g; preparable as described in Example 30(d)) and aqueous acetic acid (50%; 20 ml) was heated at 95°–100° C. for 6 hours. The solvents were evaporated under reduced pressure and the residue obtained was triturated with diethyl ether (2 ×20 ml). The resulting solid was dissolved in industrial methylated spirit (20 ml). Aqueous sodium hydroxide solution (0.5M, 22 ml) was added and the resulting mixture was stirred for 1 hour at ambient temperature and neutralised with hydrochloric acid (5M). The solvent was evaporated under reduced pressure and the residue obtained was extracted with aqueous sodium hydroxide solution (1M; 60 ml) and then acidified with hydrochloric acid (5M). The resulting precipitate was collected, washed with water (2×10 ml) and then dried to give (E)-2-benzyl-3-[2-butyl-4-chloro-1-[4-(2-hydroxy-3,4-dioxocyclobut-1 -en-1-yl)benzyl]-1H-imidazol-5-yl] propenoic acid, an active compound of the present invention, as a solid (0.54 g; m.p. 155°–160° C.).

We claim:

1. A 3-[4'-(2-Ethyl-5,7-dimethyl-3H-imidazo[4,5-b]pyrid-3-ylmethyl)biphenyl-2-yl]-4-hydroxycyclobut-3-ene-1,2-dione or a pharmaceutically acceptable salt thereof.

2. The compound according to claim 1, wherein said compound is the sodium salt of 3-[4'-(2-ethyl-5,7-dimethyl-3H-imidazo[4,5-b]pyrid-3-ylmethyl)biphenyl-2-yl]-4-hydroxycyclobut-3-ene-1,2-dione.

3. A pharmaceutical composition comprising the compound according to claim 1 in combination with a pharmaceutically acceptable carrier or diluent.

4. A method of treating hypertension comprising administering an effective amount of 3-[4'-(2-Ethyl-5,7-dimethyl-3H-imidazo[4,5-b]pyrid-3-ylmethyl)biphenyl-2-yl]-4-hydroxycyclobut-3-ene-1,2-dione or a pharmaceutically acceptable salt thereof, to a human in need of such treatment.

5. A process for preparing 3-[4'-(2-Ethyl-5,7-dimethyl-3H-imidazo[4,5-b]pyrid-3-ylmethyl)biphenyl-2-yl]-4-hydroxycyclobut-3-ene-1,2-dione, comprising hydrolyzing a compound of formula IV:

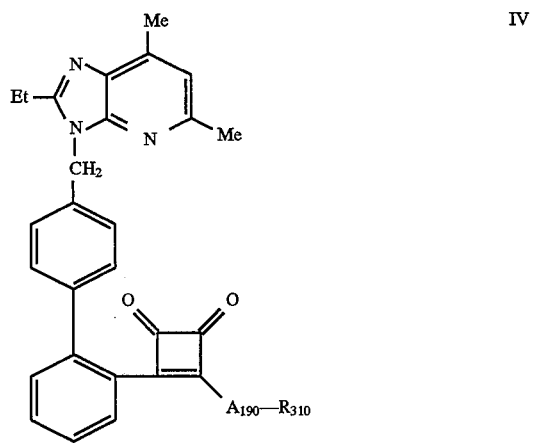

in which $Am_{190}$ is oxygen and $R_{310}$ is a lower alkyl.